United States Patent
Reno et al.

(10) Patent No.: US 10,723,684 B2
(45) Date of Patent: Jul. 28, 2020

(54) BISPHENOL ALTERNATIVE DERIVED FROM RENEWABLE SUBSTITUTED PHENOLICS AND THEIR INDUSTRIAL APPLICATION

(71) Applicants: UNIVERSITY OF DELAWARE, Newark, DE (US); THE UNITED STATES OF AMERICA AS REPRESENTED BY THE SECRETARY OF THE ARMY, Aberdeen Proving Ground, MD (US); ROWAN UNIVERSITY, Glassboro, NJ (US)

(72) Inventors: Kaleigh Havery Reno, Newark, DE (US); Joseph Francis Stanzione, III, Wilmington, DE (US); Richard Patrick Wool, Newark, DE (US); Joshua M. Sadler, Middle River, MD (US); John Joseph Lascala, Wilmington, DE (US); Eric David Hernandez, Blackwood, NJ (US)

(73) Assignees: UNIVERSITY OF DELAWARE, Newark, DE (US); THE UNITED STATES OF AMERICA AS REPRESENTED BY THE SECRETARY OF THE ARMY, Aberdeen Proving Ground, MD (US); ROWAN UNIVERSITY, Glassboro, NJ (US)

( * ) Notice: Subject to any disclaimer, the term of this patent is extended or adjusted under 35 U.S.C. 154(b) by 216 days.

(21) Appl. No.: 15/313,656

(22) PCT Filed: May 27, 2015

(86) PCT No.: PCT/US2015/032583
§ 371 (c)(1),
(2) Date: Nov. 23, 2016

(87) PCT Pub. No.: WO2015/183892
PCT Pub. Date: Dec. 3, 2015

(65) Prior Publication Data
US 2017/0210689 A1    Jul. 27, 2017

Related U.S. Application Data

(60) Provisional application No. 62/003,115, filed on May 27, 2014.

(51) Int. Cl.
C08G 59/24    (2006.01)
C08G 59/32    (2006.01)
(Continued)

(52) U.S. Cl.
CPC ............ *C07C 43/295* (2013.01); *C07C 41/09* (2013.01); *C08F 222/10* (2013.01);
(Continued)

(58) Field of Classification Search
None
See application file for complete search history.

(56) References Cited

U.S. PATENT DOCUMENTS 2,445,292 A * 7/1948 Lewis ................ C08G 16/0225
524/14
3,787,451 A * 1/1974 Mah ..................... C07D 303/24
525/524

(Continued)

FOREIGN PATENT DOCUMENTS

| GB | 920520 A | * | 3/1963 | .......... C08G 59/245 |
| JP | 2007139993 A | * | 6/2007 | ............. G03G 5/147 |
| WO | 2012149340 A1 | | 11/2012 | |

OTHER PUBLICATIONS

International Preliminary Report on Patentability for PCT/US2015/032583, dated Dec. 8, 2016, 15 pages.

(Continued)

*Primary Examiner* — Michael J Feely
(74) *Attorney, Agent, or Firm* — RatnerPrestia

(57) ABSTRACT

A compound is provided according to structure 4, (4) wherein n has a value from 0 to 48 and Z is hydroxyl or a benzene ring bearing substituents $R_{11}$-$R_{15}$, wherein $R_1$-$R_{15}$ are each individually selected from the group consisting of H, allyl, alkyl, alkoxy, phenyl, phenoxy, halide, hydroxyl, glycidyl, (meth)acryloyl, 3-(meth)acryloyl-2-hydroxy-1-propoxy, 2,3-epoxypropyl, maleate, and structure (a) wherein at least one of $R_1$-$R_5$, at least one of $R_6$-$R_{10}$, and at least one of $R_{11}$-$R_{15}$ is hydroxyl or an ether or ester derived from it and one of the $R_6$-$R_{10}$ groups is replaced by a direct bond to the CXY group.

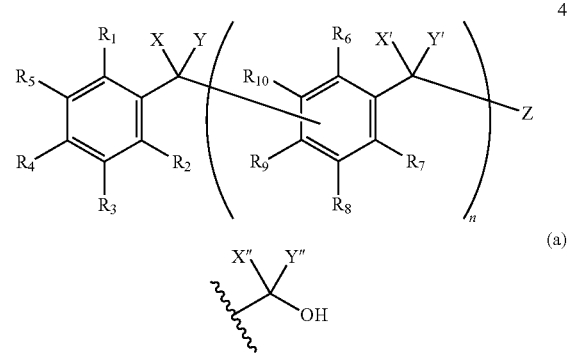

46 Claims, No Drawings

(51) Int. Cl.
*C08G 59/06* (2006.01)
*C08L 63/10* (2006.01)
*C08L 63/00* (2006.01)
*C08L 55/00* (2006.01)
*C08L 31/02* (2006.01)
*C08L 31/00* (2006.01)
*C08L 29/10* (2006.01)
*C08L 29/00* (2006.01)
*C07C 69/00* (2006.01)
*C07C 43/215* (2006.01)
*C07C 43/20* (2006.01)
*C07C 43/295* (2006.01)
*C08G 63/193* (2006.01)
*C08G 64/06* (2006.01)
*C08G 59/50* (2006.01)
*C08G 18/32* (2006.01)
*C08G 63/547* (2006.01)
*C08G 64/28* (2006.01)
*C07C 41/09* (2006.01)
*C08F 222/10* (2006.01)
*C08G 18/76* (2006.01)

(52) U.S. Cl.
CPC ..... *C08G 18/3215* (2013.01); *C08G 18/3243* (2013.01); *C08G 18/7621* (2013.01); *C08G 59/063* (2013.01); *C08G 59/245* (2013.01); *C08G 59/5026* (2013.01); *C08G 63/193* (2013.01); *C08G 63/547* (2013.01); *C08G 64/06* (2013.01); *C08G 64/28* (2013.01)

(56) References Cited

U.S. PATENT DOCUMENTS

| | | | | |
|---|---|---|---|---|
| 4,251,414 A | * | 2/1981 | Nakada | C08G 59/027 204/501 |
| 4,970,287 A | * | 11/1990 | Blakeney | C08G 8/24 430/192 |
| 5,096,762 A | * | 3/1992 | Yoshida | C08L 63/00 257/793 |
| 5,107,068 A | * | 4/1992 | Ozaki | C08G 18/4027 521/73 |
| 5,736,292 A | * | 4/1998 | Ida | C07C 39/15 430/165 |
| 6,475,693 B1 | * | 11/2002 | Susukida | G03F 7/0226 430/190 |
| 6,537,546 B2 | | 3/2003 | Echigo et al. | |
| 7,132,575 B2 | | 11/2006 | Carvill et al. | |
| 7,619,056 B2 | | 11/2009 | East et al. | |
| 8,227,561 B1 | | 7/2012 | Carlson et al. | |
| 8,263,521 B2 | | 9/2012 | Terajima et al. | |
| 2003/0069384 A1 | | 4/2003 | McCarthy et al. | |
| 2007/0048636 A1 | | 3/2007 | Qi et al. | |
| 2009/0030106 A1 | | 1/2009 | Jacobine et al. | |
| 2009/0118436 A1 | | 5/2009 | Niitani | |
| 2009/0182175 A1 | | 7/2009 | Yoshitomo et al. | |
| 2009/0258951 A1 | * | 10/2009 | Hsu | A61K 31/085 514/717 |
| 2010/0197848 A1 | | 8/2010 | Verghese et al. | |
| 2010/0280242 A1 | | 11/2010 | Hedrick et al. | |
| 2013/0130345 A1 | | 5/2013 | Thai et al. | |
| 2013/0261323 A1 | | 10/2013 | Peters et al. | |
| 2016/0272854 A1 | * | 9/2016 | Wakioka | C09J 7/00 |

OTHER PUBLICATIONS

International Search Report and Written Opinion of the International Searching Authority for International Application No. PCT/US15/32583, dated Aug. 14, 2015, 18 pages.

Reno et al., "Tackling toxicity: Designing a BPA alternative from lignin", American Cheical Society National Meeting, Dallas, Texas, Mar. 16, 2014, 14 pages.

Hernandez et al., "Bio-based epoxy resins from lignin model compounds: Renewable EPA substitues", Abstract of poster presentation at the American Chemical Society Green Chemisty and Engineering Conference, Bethesda, MD, Jun. 18, 2014, 1 page.

Hernandez et al., "Bio-based Epoxy Resinis from Lignin Model Compunds: Renewable BPA Substitutes", 2014 ACS GC and E Poster presented at the American Chemical Society Green Chemistry and Engineering Conference, Bethesda, MD, Jun. 18, 2014, 1 page.

Sadler et al., "Bio-based Thermosetting Eposy Resins Derived from Vanillyl Alcohol", ACS National Meeting 2015 Presentation EDH, oral presetnation at the American Chemical Society National Meeting, Denver, CO, Mar. 22, 2015, 23 pages.

Maylemans et al., "Synthesis of Renewable Bisphenols from Creosol", ChemSusChem, 2012, vol. 5, pp. 206-210.

* cited by examiner

BISPHENOL ALTERNATIVE DERIVED FROM RENEWABLE SUBSTITUTED PHENOLICS AND THEIR INDUSTRIAL APPLICATION

CROSS REFERENCE TO RELATED APPLICATIONS

The present application is a National Phase filing of International application No. PCT/US15/032583, filed 27 May 2015, and claims priority to U.S. Provisional Application Ser. No. 62/003,115, filed on 27 May 2014, the contents of which applications are incorporated fully herein by reference for all purposes.

GOVERNMENT SUPPORT CLAUSE

This invention was made with U.S. government support under DOD/ARL Grant # W911NF-06-2-001. The government may have certain rights in the invention.

BACKGROUND OF THE INVENTION

Bisphenols such as bisphenol A (4,4'-isopropylidenephenol) (BPA) are used extensively in plastics and composites due to its aromaticity that provides high mechanical strength to BPA derived polymers. Approximately 6.5 million tons are produced a year globally for the production of thermosets and thermoplastics. Industrially, these polymers are used in the manufacturing of goods such as metal food can epoxy resin linings and polycarbonate containers. BPA is a known endocrine disruptor and is derived from petroleum, a non-renewable resource. Therefore, BPA alternatives with fewer health concerns derived from sustainable renewable alternatives would have an immeasurable impact on the polymer, coatings, adhesives, and additives industries.

In recent studies, low dose exposure to BPA during fetal development and puberty caused lifelong physical and mental health such as birth defects, obesity, thyroid issues, and cause changes in reproductive development, to name a few. As an indication of how much humans are exposed to BPA, it is estimated that over 90% of the population of industrial countries have BPA and its metabolites in their urine. Most recently, studies suggest there may be a link between autism spectrum disorder in children and BPA exposure.

Additionally, currently used industrial bisphenols are derived from petroleum, a non-renewable resource on the time scale of consumption. Utilizing renewable sources of aromaticity, such as lignin, the second most abundant natural polymer rich in aromatic content, holds the potential to be a low cost sustainable alternative to petroleum feedstocks. On average, 70 million tons of lignin is produced as a waste product of the paper and pulping industry. The breakdown of lignin into monophenolics through processes such as pyrolysis is a promising feedstock of functionalized phenols that can be used as is or processed into specialty chemicals.

Successful bisphenol alternatives must provide comparable or improved thermomechanical and optical properties, function as a drop in replacement, and have decreased toxicity and endocrine disruption potential. Many current alternatives provide similar properties but are difficult to synthesize and require expensive processing steps. These intensive synthesis steps limit their application as industrial alternatives to bisphenols. Other alternatives are derived from natural resources; however, these resources cannot sustain the production quotas necessary for industrial production. Furthermore, many other bisphenol alternatives are synthesized from toxic or volatile monomers such as formaldehyde and acetone.

Additionally, many syntheses use electrochemistry, harsh mineral acids, or complex catalyst systems for the synthesis of bisphenol alternatives, which may lead to low yields, damaged processing equipment, and high catalyst cost. Methods and compositions capable of addressing one or more of these issues would be a welcome addition to the state of the art.

SUMMARY OF THE INVENTION

The invention provides a compound according to structure 4,

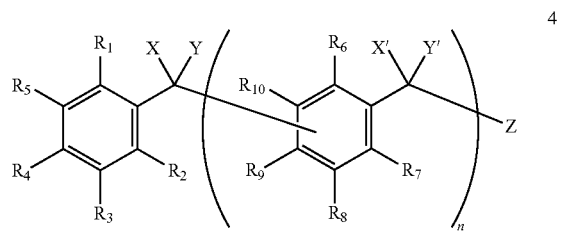

wherein n has a value from 0 to 48 and Z is hydroxyl or a benzene ring bearing substituents $R_{11}$-$R_{15}$, wherein $R_1$-$R_{15}$ are each individually selected from the group consisting of H, allyl, alkyl, alkoxy, phenyl, phenoxy, halide, hydroxyl, glycidyl, (meth)acryloyl, 3-(meth)acryloyl-2-hydroxy-1-propoxy, 2,3-epoxypropyl, maleate, and structure (a)

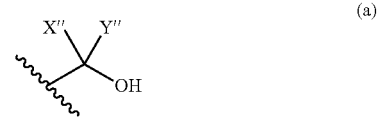

wherein at least one of $R_1$-$R_5$, at least one of $R_6$-$R_{10}$, and at least one of $R_{11}$-$R_{15}$ is hydroxyl or an ether or ester derived from it;

wherein one of the $R_6$-$R_{10}$ groups is replaced by a direct bond to the CXY group;

wherein the repeat units comprising $R_6$-$R_{10}$, X' and Y' may be the same or different from each other when n>1;

wherein X, X', X", Y, Y', and Y" are each individually selected from the group consisting of H, alkyl, aryl, halo, hydroxyl phenyl, substituted phenyl, or wherein one or more of X and Y, X' and Y', and X" and Y" together constitute =O;

excluding compounds according to structure 4 comprising two or fewer glycidyl, (meth)acryloyl and/or 3-(meth)acryloyl-2-hydroxy-1-propoxy substituents in total and in which the only phenolic moieties present are formed from one or more of vanillyl alcohol, hydroquinone, bisphenol A, bisphenol AP, bisphenol AF, bisphenol B, bisphenol BP, bisphenol C, bisphenol E, bisphenol F, bisphenol G, bisphenol M, bisphenol S, bisphenol P, bisphenol PH, bisphenol TMC, bisphenol Z, condensates consisting of only 1 vanillyl alcohol unit and only 1 cresol unit, and condensates consisting of only 1 vanillyl alcohol unit and only 1 phenol unit, except that the following are not excluded:

A) compounds bearing two or fewer meth(acryloyl) and/or 3-(meth)acryloyl-2-hydroxy-1-propoxy substituents, separately or in combination, in which the compounds comprise one or more moieties formed from vanillyl alcohol;

B) compounds bearing two or fewer glycidyl substituents and comprising three or more vanillyl alcohol, hydroquinone, or cresol moieties; and C) compounds bearing two or fewer glycidyl, (meth)acryloyl and/or 3-(meth)acryloyl-2-hydroxy-1-propoxy substituents, separately or in combination, in which the only phenolic moieties present are formed from vanillyl alcohol and one or more of bisphenol A, bisphenol AP, bisphenol AF, bisphenol B, bisphenol BP, bisphenol C, bisphenol E, bisphenol F, bisphenol G, bisphenol M, bisphenol S, bisphenol P, bisphenol PH, bisphenol TMC, and bisphenol Z.

The invention also provides polymers or oligomers including two or more units of the compound according to structure 4, wherein each unit is joined to one or more other units by a $CH_2CH(OH)CH_2$ group attached to phenolic oxygen atoms on the units.

The invention also provides polymers or oligomers including two or more units of the compound according to structure 4, wherein each unit is joined to phenolic oxygen atoms on one or more other units by a moiety of the following structure

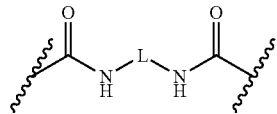

wherein L is a residue of an organic compound including two or more isocyanate groups, and wherein more than one type of L may be present in the polymer or oligomer.

The invention also provides polymers or oligomers including two or more units of the compound according to structure 4, wherein each unit is joined to phenolic oxygen atoms on one or more other units by a moiety of the following structure

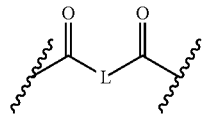

wherein L is a residue of an organic compound including two or more carboxylic acid groups, and wherein more than one type of L may be present in the polymer or oligomer.

The invention also provides a process for producing a compound according to according to structure 4, including contacting one or more phenols bearing a CXYOH substituent and optionally at least one other substituent on the ring, and optionally one or more substituted phenols lacking a CXYOH substituent on the ring, with an acidic ion exchange resin under conditions effective to form the compound.

DETAILED DESCRIPTION OF THE INVENTION

The invention provides phenolic blocks comprising one or more phenolic moieties, and products derived from these blocks. When two or more phenolic moieties are present in a phenolic block, they are joined by a substituted or unsubstituted methylene group. Phenolic blocks with controlled regioselectivity and number of phenolic repeat units may be synthesized according to the invention from substituted hydroxymethyl phenols, optionally combined with substituted phenols lacking hydroxymethyl groups. The phenolic blocks hold promise as sustainable, less toxic, drop-in alternatives to industrially relevant bisphenols. The phenolic blocks are potentially derived from renewable resources, and can be prepared with controlled regioselectivity and oligomerization. Facile synthesis of these alternatives and their industrial application in thermoplastics and thermosets is presented.

The phenolic blocks can be derivatized to provide products referred to herein as "reactive functionalized phenolics." For example, the reactive functional groups may be epoxy and/or (meth)acryloyl groups, the latter term meaning methacryloyl or acryloyl. The phenolic blocks and/or reactive functionalized phenolics can in turn be converted to polymers for thermoset and thermoplastic applications. Examples include poly(meth)acrylates or vinyl ester resins, epoxy resins, polycarbonates, polyurethanes, and unsaturated polyesters. These may be used in a variety of applications, including composites and coatings.

The phenolic blocks of the invention, and the reactive functionalized phenolics prepared from them, are according to structure 4,

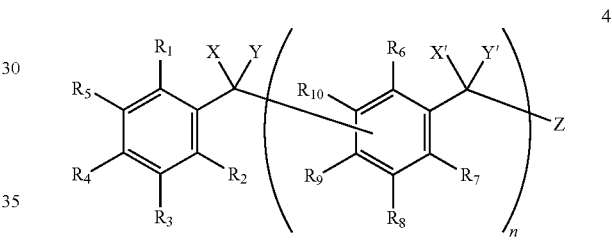

wherein n has a value from 0 to 48 and Z is hydroxyl or a benzene ring bearing substituents $R_{11}$-$R_{15}$, wherein $R_1$-$R_{15}$ are each individually selected from the group consisting of H, allyl, alkyl, alkoxy, phenyl, phenoxy, halide, hydroxyl, glycidyl, (meth)acryloyl, 3-(meth)acryloyl-2-hydroxy-1-propoxy, 2,3-epoxypropyl, maleate, and structure (a)

wherein at least one of $R_1$-$R_5$, at least one of $R_6$-$R_{10}$, and at least one of $R_{11}$-$R_{15}$ is hydroxyl or an ether or ester derived from it;

wherein one of the $R_6$-$R_{10}$ groups is replaced by a direct bond to the CXY group;

wherein the repeat units comprising $R_6$-$R_{10}$, X' and Y' may be the same or different from each other when n>1; and wherein X, X', X", Y, Y', and Y" are each individually selected from the group consisting of H, alkyl, aryl, halo, hydroxyl phenyl, substituted phenyl, or wherein one or more of X and Y, X' and r, and X" and Y" together constitute =O.

As used herein, a "maleate" substituent on a benzene ring means a monoester of a phenol with maleic acid. It can be formed by opening the anhydride ring of maleic anhydride with a phenol.

The skilled person will recognize that in structure 4 above, one of the $R_6$ to $R_{10}$ groups is in fact not present on each ring, but is instead replaced by a direct bond to the CXY group.

In some embodiments, the compounds according to structure 4 exclude ones in which the only phenolic moieties present are formed from one or more of vanillyl alcohol, hydroquinone, bisphenol A, bisphenol AP, bisphenol AF, bisphenol B, bisphenol BP, bisphenol C, bisphenol E, bisphenol F, bisphenol G, bisphenol M, bisphenol S, bisphenol P, bisphenol PH, bisphenol TMC, bisphenol Z, condensates consisting of only 1 vanillyl alcohol unit and only 1 cresol unit, and condensates consisting of only 1 vanillyl alcohol unit and only 1 phenol unit, and/or such compounds substituted with two or fewer glycidyl, (meth)acryloyl and/or 3-(meth)acryloyl-2-hydroxy-1-propoxy substituents in total. In some embodiments, compounds according to structure 4 exclude ones that comprise any amount of any one or more of these phenolic moieties.

Nonetheless, in some embodiments the following exceptions apply to the foregoing exclusions:

A) compounds bearing two or fewer meth(acryloyl) and/or 3-(meth)acryloyl-2-hydroxy-1-propoxy substituents, separately or in combination, in which the compounds comprise one or more moieties formed from vanillyl alcohol;

B) compounds bearing two or fewer glycidyl substituents and comprising three or more vanillyl alcohol, hydroquinone, or cresol moieties; and C) compounds bearing two or fewer glycidyl, (meth)acryloyl and/or 3-(meth)acryloyl-2-hydroxy-1-propoxy substituents, separately or in combination, in which the only phenolic moieties present are formed from vanillyl alcohol and one or more of bisphenol A, bisphenol AP, bisphenol AF, bisphenol B, bisphenol BP, bisphenol C, bisphenol E, bisphenol F, bisphenol G, bisphenol M, bisphenol S, bisphenol P, bisphenol PH, bisphenol TMC, and bisphenol Z.

As used herein, a "condensate" of phenolic compounds is one where a CXYOH group on the benzene ring of one compound links to the benzene ring of another with loss of water.

In some embodiments, one or more of the following limitations, in any combination, may apply to the compound according to structure 4. The groups X, X', X", Y, Y', and Y" are all H. All of groups $R_1$ to $R_{15}$ are selected from the group consisting of H, alkyl, hydroxyl, glycidyl, (meth)acryloyl, 3-(meth)acryloyl-2-hydroxy-1-propoxy, hydroxymethyl, and maleate. At least one of $R_{11}$-$R_{15}$ is structure (a). At least one of $R_1$-$R_{15}$ is glycidyl. At least one of $R_1$-$R_5$, at least one of $R_6$-$R_{10}$, and at least one of $R_{11}$-$R_{15}$ is hydroxyl or an ether or ester derived from it. At least one other (i.e., not the hydroxyl, ether or ester) of $R_1$-$R_5$, at least one other of $R_6$-$R_{10}$, or at least one other of $R_{11}$-$R_{15}$ is not H. The value of n is 0, or is in a range from 1 to 5.

Alternatively, or in addition to this first groups of limitations that may be required in some embodiments, the following limitations may also or instead be required in some embodiments, in any combination with each other and/or with limitations from the first group.

In some embodiments, the invention does not encompass one or more of the following compounds according to structure 4, and/or does not encompass oligomers or polymers that include two or more units of such compounds linked by a $CH_2CH(OH)CH_2$ group attached to phenolic oxygen atoms on the units.

Vanillyl alcohol
  Either vanillyl alcohol or a dimer thereof, bearing two or fewer epoxy groups, each in a substituent thereon Compounds according to structure 4 having either one or two benzene rings, and meeting one or more of the following limitations, in any combination: no epoxy groups, no (meth)acryloyl groups, no allyl groups, and/or no maleate groups Compounds according to structure 4 having either one or two benzene rings and bearing exactly two epoxy groups, each in a substituent thereon The phenolic block and/or any reactive functionalized phenolic or product made from either or both of these, may in some embodiments employ phenolic blocks in which all of the phenolic rings are produced from condensation of one or more of vanillyl alcohol, 4-hydroxy-3-methoxy-α-methylbenzyl alcohol and 4-hydroxy-3-methoxy-α,α-dimethylbenzyl alcohol, either with itself (or themselves, in any combination) or with one or more of guaiacol, eugenol, 4-ethylguaiacol, 4-propylguaiacol, vanillin, creosol, catechol or phenol, in any combination. All permutations and combinations based on these materials are contemplated according to the invention.

Some specific embodiments are as follows. It is possible to prepare vinyl esters from diepoxy vanillyl alcohol, diepoxy catechol, and other epoxies by methacrylating the epoxies with methacrylic acid at approximately 90° C. using various catalysts, such as AMC-2. One can prepare mixed methacrylate/epoxy single aromatic species by using less than stoichiometric amounts of methacrylic acid. One can also directly methacrylate the hydroxyl groups of single aromatic compounds using methacrylic anhydride to produce vanillyl alcohol dimethacrylate, catechol dimethacrylate, and other such molecules. One can prepare polycarbonates by replacing BPA with any catechol molecule and polymerizing with phosgene, p-nitrochlorophenol, etc. One can prepare unsaturated polyesters through reaction of dihydroxy single aromatic species, for example catechol and vanillyl alcohol, with maleic anhydride, phthalic anhydride, and other dihydroxy species in a typical polyester reaction at elevated temperatures. One can prepare polyurethane oligomers and polymers by reaction of dihydroxy single aromatic species, for example catechol and vanillyl alcohol, with diisocyanates, for example toluene diisocyanate and isophorone diisocyanate, under well-established conditions.

In some embodiments, one or more of the following may be true. At least one of $R_{11}$-$R_{15}$ in structure 4 is structure (a). In some embodiments, X, X', X", Y, Y', and Y" are all H. At least one of $R_1$-$R_{15}$ is glycidyl. At least one of $R_1$-$R_{15}$ is (meth)acryloyl or 3-(meth)acryloyl-2-hydroxy-1-propoxy. At least one of $R_1$-$R_5$, at least one of $R_6$-$R_{10}$, or at least one of $R_{11}$-$R_{15}$ is neither H nor OH. The value of n is 0 and Z is said benzene ring bearing substituents $R_{11}$-$R_{15}$. Any compound according the invention that contains at least one epoxy group can be reacted according to the invention with a diamine or other epoxy curing agent. Similarly, any compound according the invention that contains at least one (meth)acryloyl, maleate, or allyl group can be cured according to the invention by free radical polymerization.

In some embodiments, the invention provides a polymer or oligomer comprising two or more units of a compound according to structure 4, wherein each unit is joined to one or more other units by a $CH_2CH(OH)CH_2$ group attached to phenolic oxygen atoms on the units, and wherein at least one of $R_1$-$R_{15}$ on at least one of the units is glycidyl. For such polymers or oligomers, one or more of the following, in any combination, may be true. At least one of $R_1$-$R_{15}$ is (meth)acryloyl or 3-(meth)acryloyl-2-hydroxy-1-propoxy. The value of n is 0 and Z is the aforementioned benzene ring bearing substituents $R_{11}$-$R_{15}$.

In some embodiments, the invention provides a polymer or oligomer comprising two or more units of a compound according to structure 4, wherein each unit is joined to one or more other units by a $CH_2CH(OH)CH_2$ group attached to phenolic oxygen atoms on the units. For such polymers or oligomers, one or more of the following, in any combination, may be true. At least one of $R_1$-$R_{15}$ on at least one of the units is 3-(meth)acryloyl-2-hydroxy-1-propoxy. At least one of $R_1$-$R_{15}$ on at least one of the units is (meth)acryloyl. At least one of $R_1$-$R_{15}$ on at least one of the units is allyl. At least one of $R_1$-$R_{15}$ on at least one of the units is glycidyl. For the cases where 3-(meth)acryloyl-2-hydroxy-1-propoxy and/or (meth)acryloyl and/or allyl are present, the polymers or oligomers may take part in chain growth polymerization.

In some embodiments, the invention provides a polymer formed by self-condensation of a compound according to structure 4 in which at least one of $R_1$-$R_5$, at least one of $R_6$-$R_{10}$, and at least one of $R_{11}$-$R_{15}$ is hydroxyl, in particular a compound in which n=0 and Z is said benzene ring bearing substituents $R_{11}$-$R_{15}$. In either case, when at least at least one of $R_1$-$R_{15}$ is CXYOH, for example $CH_2OH$, the invention provides a crosslinked polymer of unmeasurable molecular weight or a linear or branched polymer with molecular weight greater than 5,000 g/mol, formed by self-condensation of the compound.

In some embodiments, the invention provides a polymer or oligomer comprising two or more units of a compound according to structure 4, wherein each unit is joined to phenolic oxygen atoms on one or more other units by a moiety of the following structure

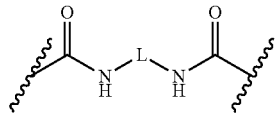

wherein L is a residue of an organic compound comprising two or more isocyanate groups, for example toluene diisocyanate and isophorone diisocyanate, and wherein more than one type of L may be present in the polymer or oligomer.

In some embodiments, the invention provides a polymer or oligomer comprising two or more units of a compound according to structure 4, wherein each unit is joined to phenolic oxygen atoms on one or more other units by a moiety of the following structure

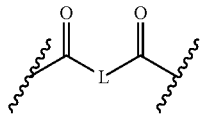

wherein L is a residue of an organic compound comprising two or more carboxylic acid groups, and wherein more than one type of L may be present in the polymer or oligomer.

Examples of compounds comprising two or more carboxylic acid include phthalic acid, terephthalic acid, maleic acid, fumaric acid, azelaic acid, adipic acid, succinic acid, and itaconic acid, and their associated anhydrides. In some embodiments, the polymer or oligomer comprises one or more olefinically unsaturated units, for example from maleic acid. Polymers or oligomers can be made by chain growth polymerization of such a polymer or oligomer.

In some embodiments, the invention provides a polycarbonate polymer/oligomer prepared by polycondensation of a compound according to structure 4, especially one in which n=0 and Z is a benzene ring bearing substituents $R_{11}$-$R_{15}$, with phosgene, a phosgene equivalent, or a chloroformate, for example p-nitrophenyl chloroformate.

Preparing the Phenolic Blocks

In some embodiments, the use of acidic ion exchange resins allows for facile catalyst removal and reuse in addition to allowing for continuous flow processing such as fluidized bed reactors. Further control of oligomerization and regioselectivity is achieved by tuning the reaction environment. Below a critical stoichiometry of 4.5 equivalents of guaiacol per equivalent of vanillyl alcohol, oligomerization is favored, whereas high yields of bisphenolics are achieved above that stoichiometry. This applies also to the formation of bisphenolics from analogs of vanillyl alcohol and guaiacol. Respectively, these are substituted phenols bearing a CXYOH substituent and optionally at least one other substituent on the ring, and substituted phenols lacking a CXYOH substituent on the ring. It is generally possible to produce a reaction product containing at least 90 mol % of bisphenolic compound, i.e., a compound according to structure 4 in which n=0 and Z is a benzene ring bearing substituents $R_{11}$-$R_{15}$, Regioselectivity can be manipulated through the presence or absence of water during synthesis. Removing water during the reaction favors p,p connectivity, as seen in examples 13 and 14, while adding water and/or minimizing the loss of water favors non-p,p connectivity. As used herein, "p,p connectivity" means that the linking group between adjacent phenolic rings is attached at the para position of each ring, relative to the phenolic hydroxyl. Controlling stoichiometry and regioselectivity provides handles for tuning desirable properties of the final product containing these bisphenol alternatives. In some embodiments, at least 40% of the connections between phenolic moieties are p,p, or at least 45%, or at least 50%, or at least 55%, or at least 60%, or at least 65%, or at least 70%, or at least 75%, or at least 80%, or at least 85%. In some embodiments, processes according to the invention eliminate the need for volatile reactants by using solids or low volatility liquids as reactants while maintaining facile synthesis.

In some embodiments, the invention provides a process for producing a compound according to structure 4, for example one in which n=0 and Z is a benzene ring bearing substituents $R_{11}$-$R_{15}$. The process comprises contacting one or more phenols bearing a CXYOH substituent and optionally at least one other substituent on the ring, and optionally one or more substituted phenols lacking a CXYOH substituent on the ring, with an acidic ion exchange resin under conditions effective to form the compound. In some cases, no substituted phenol lacking a CXYOH substituent on the ring is present. In some cases, one or more substituted phenols lacking a CXYOH substituent on the ring is/are present, relative to the one or more phenols bearing a CXYOH substituent and optionally at least one other substituent on the ring, at a molar ratio greater than 1.0 and at most 4.5.

In some embodiments, the invention provides a process for producing a compound according to structure 4, comprising contacting one or more phenols bearing a CXYOH substituent and optionally at least one other substituent on the ring, and one or more substituted phenols lacking a CXYOH substituent on the ring, with an acidic ion exchange resin under conditions effective to form the compound;

wherein the one or more substituted phenols lacking a CXYOH substituent on the ring is/are present, relative to the one or more phenols bearing a CXYOH substituent and optionally at least one other substituent on the ring, at a molar ratio greater than 4.5;
in which at least 90 mol % of the product has n=0 and Z is a benzene ring bearing substituents $R_{11}$-$R_{15}$.

In some embodiments, the invention provides a process for producing a compound according to structure 21,

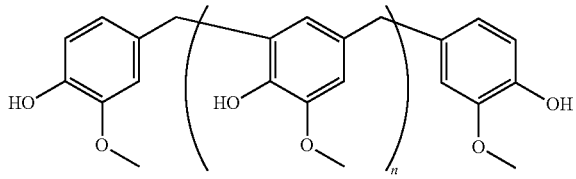

21 comprising reacting vanillyl alcohol with excess guaiacol in the presence of an acidic ion exchange resin, wherein $1<n\leq 48$ on average and the molar ratio of guaiacol to vanillyl alcohol is $\leq 4.5$.

In some embodiments, the invention provides a process for producing a compound according to structure 21, comprising reacting vanillyl alcohol with excess guaiacol in the presence of an acidic ion exchange resin, wherein $0\leq n\leq 1$ on average and the molar ratio of guaiacol to vanillyl alcohol is $\geq 4.5$. In some embodiments, the invention provides a process for producing a compound according to structure 21, comprising reacting vanillyl alcohol with excess guaiacol in the presence of an acidic ion exchange resin with removal of water during the reaction to promote p,p connectivity.

Products Prepared from the Phenolic Blocks

Scheme 1 shows various products synthesized according to the invention in the exemplary case where the phenolic block is bisguaiacol F (BGF), shown as Product 1. This example has two phenolic groups in the phenolic block (n=0 and Z=substituted benzene in structure 4), but it is to be understood that phenolic blocks according the invention may have three, four, or any number up to 50 phenolic residues. In some embodiments, the number of residues is in a range from 2 to 10, or from 2 to 3, or from 3 to 10, or from 3 to 5. Product 1 has p,p connectivity, but this is only exemplary and other connectivities may be suitable and are contemplated. The chemistries shown in Scheme 1 can be applied to phenolic blocks with more than two residues and/or different connectivity and/or additional substituents on one or more of the rings, all according to the invention. The embodiments in Scheme 1 are also ones in which guaiacol, a phenol not bearing a substituted or unsubstituted benzylic hydroxyl group, is included in the condensation. This terminates the oligomer chain. In some embodiments (not shown in Scheme 1), vanillyl alcohol and/or another phenol bearing a substituted or unsubstituted benzylic hydroxyl group is condensed without guaiacol or an analog thereof, leaving at least one substituted or unsubstituted benzylic hydroxyl group on the phenolic block.

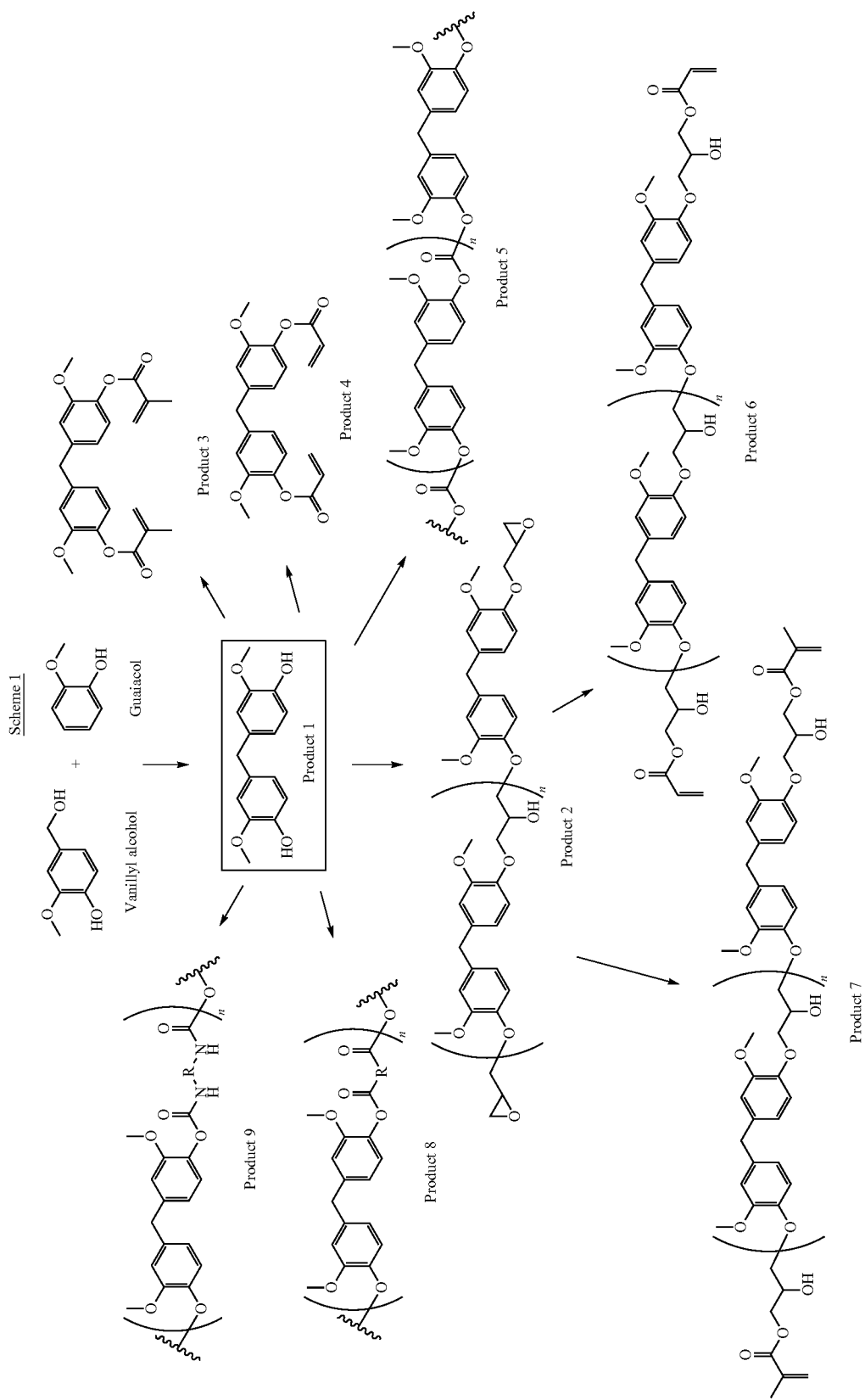

As shown in Scheme 1, the phenolic blocks can be converted to reactive functionalized phenolics suitable for use in a variety of applications, typically as prepolymers.

Diglycidyl ethers of substituted bisphenols (Product 2) can be synthesized from Product 1 via reaction with epichlorohydrin and a base, which may be an alkali salt, for example sodium hydroxide or potassium hydroxide. The value of n may range from 0 to 24, or from 0 to 10, or from 0 to 5, or from 0 to 3, or from 0 to 1. In some embodiments, synthesis of these diglycidyl ethers is carried out with at least two equivalents of epichlorohydrin (preferably 10 or 30 equivalents) to minimize oligomerization and thereby produce epoxies with average n values less than 1, and with at least two stoichiometric equivalents of base (preferably 3-6) for every equivalent of substituted bisphenol. The reaction of Product 1 with epichlorohydrin can be catalyzed by a phase transfer catalyst, which may be a quaternary ammonium salt (for example n-butyl ammonium bromide), preferably at a concentration of 10-11 mol % of Product 1. The synthesis of Product 2 involves mixing Product 1 with epichlorohydrin at 15-60° C. preferably 20-25° C. followed by addition of the alkali base at 0-10° C. preferably 0-5° C.

Product 2 is recovered from the reaction mixture after aqueous washes to remove salts and distillation to remove epichlorohydrin. The addition of epoxide groups to the substituted bisphenol is confirmed via the presence characteristic epoxide peaks in NMR and near-IR. Epoxide equivalent weight titration as described in ASTM D-1652 is used to determine the average molecular weight per epoxide group.

Product 2 can be reacted with curing agents such as diamines to create a cross linked polymer network. Reaction of Product 2 with a diamine, for example 4,4'-diaminodicyclohexylmethane, preferably at stoichiometric equivalents based on epoxide equivalent weight and amine hydrogen equivalent weight (52.5 g/eq if 4,4'-diaminodicyclohexylmethane) can be carried out at 100-250° C. preferably 160-180° C. with a step curing procedure. The extent of cure is determined via the ratio of epoxy and amine peaks in Near-IR spectra both before and after curing. The glass transition temperature ($T_g$) of the epoxy resin can be determined via DSC. These diepoxies can also be cured with acid anhydrides in stoichiometric equivalents, creating ester linkages.

More generally, the reaction used to form the epoxy thermoset also involves at least one epoxy curing agent. Suitable curing agents for epoxies are well known in the industry. Examples include aliphatic polyamines such as diethylenetriamine (DETA), triethylenetetramine (TETA), tetraethylenepentamine (TEPA), diproprenediamine (DPDA), dimethylaminopropylamine (DEAPA); alicyclic polyamines such as N-aminoethylpiperazine (N-AEP), menthane diamine (MDA), isophoronediamine (IPDA); aliphatic aromatic amines such as m-xylenediamine (m-XDA); aromatic amines such as metaphenylene diamine (MPDA), diaminodiphenylmethane (DDM), diaminodiphenylsulfone (DDS); and mixtures thereof. Further examples of suitable curing agent include EPIKURE® Curing Agent W, AMICURE® PACM/bis-(p-aminocyclohexyl)methane. Other curing agents include nadic methyl anhydride, phthalic anhydride dicyandiamide, nadic anhydride, and dicyandiamide. These curing agents are added to epoxy resins at amounts typically at or near stoichiometry, although off-stoichiometry amounts may be useful for the creation of prepregs. Epoxy homopolymerization catalysts, for example tertiary amines such as such as benzyl dimethylamine, can also cure these epoxy resins when added in catalytic amounts, typically up to 5 wt %. All of the epoxy resins are cured by ambient, thermal, induction, electron beam, UV cure or other such standard methods whereby energy is provided to initiate the reaction between the epoxy and the curing agent/catalyst. Post-cure is typically necessary because the rate of cure slows severely upon vitrification.

Product 1 can be functionalized through a number of methods and converted to Product 3 or Product 4 to produce methacrylated and acrylated phenolics, respectively, that are capable of free radical polymerization. Product 3 is formed through the esterification of Product 1 using either methacryloyl chloride or methacrylic anhydride and a base catalyst (for example 4-(dimethylamino)pyridine and triethylamine) in an aprotic solvent (for example dichloromethane, and tetrahydrofuran). Reaction temperatures occur at preferably 20-80° C., but most preferably at 25-55° C. The synthesis of Product 4 can be carried out using similar methodology utilizing acryloyl chloride or acrylic anhydride as the (trans)esterification agents. NMR analysis shows peaks in the expected with locations, with minimal impurities. Product 2 can be converted to a (meth)acrylic ester through reaction with a slight excess of acrylic acid (Product 6) or methacrylic acid (Product 7) at 70-120° C. and preferably from 90-100° C. preferably using a catalyst, such as AMC-2 or triphenylphosphine, triphenylantimony(III), for 1-5 hours and preferably 2-3 hours with no separation. Acid number can be used to verify addition of the (meth)acrylic acid with acid number of less than 20 being ideal. NMR can be used to verify that nearly two (meth)acrylates per molecule are present.

Product 2 can be converted to an epoxy-(meth)acrylic ester through reaction with acrylic acid or methacrylic acid at 70-120° C., preferably from 90-100° C., using a catalyst, such as AMC-2 or triphenylphosphine, triphenylantimony (III), for 1-5 hours and preferably 2-3 hours with no separation. The amount of (meth)acrylic acid used is less than the stoichiometric amount of epoxy on Product 2, preferably 25-75 mol % of the stoichiometric amount. Acid number can be used to verify addition of the (meth)acrylic acid, with acid number of less than 15 being ideal. NMR can be used to verify the number of (meth)acrylates and epoxies per molecule present.

Product 8 can be synthesized under various conditions that can result in the formation of polyester or unsaturated polyester resins (UPE)s depending on the reaction composition. Product 1 is melted together in the presence or absence of another diol or polyol moiety, for example diethylene glycol, isosorbide, and propylene glycol, with a single or mixture of organic diacids, for example maleic anhydride, phthalic anhydride, terephthalic acid or adipic acid. The reaction is catalyzed using an acid catalyst, for example p-toluenesulfonic acid, AMBERLYST 15 hydrogen form or DOWEX DR-2030 hydrogen form, and can be done in the presence or absence of an azeotropic solvent, for example toluene and xylenes, to aid in water removal. The reaction temperature can be carried out at preferably 55-220° C., but most preferably 125-180° C. NMR analysis showed peaks in the expected locations for polymeric material, based on the components in the starting reaction mixture. GPC analysis showed that the preferred molecular weights are greater than 2,000 g/mol, but molecular weights above 500 g/mol are acceptable, and the most preferred molecular weights of 1,500-3,000 g/mol are also possible.

Product 9 can be synthesized using Product 1 in combination with various diisocyanates or polyisocyanates to form prepolymeric oligomers or high molecular weight polymers, depending on stoichiometric ratios. Product 1 is dissolved in solvent, for example tetrahydrofuran, chloroform, diethyl ether, with a multifunctional isocyanate, for example toluene diisocyanate, hexamethylene diisocyanate, methylene diphenyl diisocyanate, and/or isophorone diisocyanate, before adding a catalytic amount of organic base, for example triethylamine, pyridine, 1,8-diazabicyclo[5.4.0]undec-7-ene (DBU), typically at a concentration of 1-25 mol %, more typically 5-15 mol %. The preferred ratios for the synthesis of Product 9 are 25-75 mol % Product 1 and 25-75 mol % diisocyanate, more preferably a ratio of 33-67 mol % Product 1 and 33-67 mol % diisocyanate. The reaction temperature is preferably 0-125° C., more preferably 25-80° C. NMR analysis showed peaks in the expected locations for polymeric material without degradation of starting BGF ring system. GPC analysis showed that the preferred molecular weights are greater than 8,000 g/mol, but weights of 1,500-9,000 g/mol are also possible and the reaction can be completed so that the molecular weights are >12,000 g/mol.

Product 5 can be synthesized using Product 1 in the presence of phosgene or phosgene derivatives or in the presence of p-nitrophenyl chloroformate or other chloroformates. Product 1 can be dissolved in a solvent, for example 1,4-dioxane, acetonitrile, dichloromethane. In the case of liquid of solid co-reactants, the co-reactant can be dissolved in a solvent, for example 1,4-dioxane, acetonitrile, dichloromethane. These solutions could be added to a catalytic amount of organic base including, but not limited to pyridine, 4-(dimethylamino)pyridine, 1-methylimidazole, 2-methylimidazole, in concentrations of preferably 0.5-10 mol %, but most preferably in 1-5 mol %. A stoichiometric amounts of a second organic base, for example trimethylamine, pyridine, could also be added. Preferred reaction temperatures are 0-100° C., more preferably 15-40° C. The reaction may be conducted in contact with atmospheric air, but are preferably done under an inert atmosphere. Polymeric material can be recovered by addition of an antisolvent, but other such techniques are possible including filtration, vacuum distillation, chromatography, and flash chromatography. GPC, FTIR and NMR analyses showed peaks in the expected locations for polymeric material without degradation of the starting bisphenolic structure. These results validated that the polymerization is insensitive to the specific structure of Product 1; thus, would work for any variants of Product 1. However, higher molecular weight polymers can be achieved via higher purity reactants, reagents, and optimized reaction conditions. Preferred number average molecular weights (measured by GPC) are greater than 6,000 g/mol, but number average molecular weights of 500-12,000 g/mol are also possible and the reaction can be completed so that the number average molecular weights are greater than 12,000 g/mol. A dispersity of 1-5 is preferred, more preferably 1.5-2.5. In one example, a $T_g$ of 110° C. was determined via DSC (10° C./min heating rate). Typically, the glass transition temperature will be in the range of 25-150° C., more typically 75-150° C.

Uses of the Phenolic Blocks and Reactive Functionalized Phenolics

Any of the phenolic blocks and/or reactive functionalized phenolics, prepared and cured as discussed above with respect to the exemplary embodiments in Scheme 1, may be used to prepare thermosetting compositions, examples of which include coatings and composite materials.

Coatings made from the cured phenolic blocks and/or reactive functionalized phenolics may contain solvents, for example methyl ethyl ketone, acetone, tert-butyl acetate, and additional additives such as fibers, clays, silicates, fillers, whiskers or other conventional filler, reinforcing materials, including their nanometer scale analogues, pigments such as titanium dioxide, iron oxides, and carbon black, corrosion inhibitors such as zinc phosphate. Additional additives that may be employed include flow additives, film formers, defoamers, coupling agents, antioxidants, stabilizers, flame retardants, reheating aids, plasticizers, flexibilizers, anti-fogging agents, nucleating agents, and combinations thereof. The coatings can be applied using various methods, for example brush, roller, or sprayer. The coatings are typically cured under ambient conditions, but may be cured under a variety of other conditions, for example oven curing at elevated temperature. The phenolic blocks and/or reactive functionalized phenolics may be cured by any of the methods and chemistries described herein.

Composites made from the cured phenolic blocks and/or reactive functionalized phenolics may contain additives such as fibers, clays, silicates, fillers, whiskers or other conventional filler or reinforcing materials, including nanomaterials. Typical fibers used for such composites include, but are not limited to, E-glass, S-glass, KEVLAR®, carbon fiber, and ultra-high molecular weight polyethylene. Additional additives may be employed in conventional amounts and may be added directly to the process during formation of the composite. Such additional additives may include, for example, colorants, pigments, carbon black, fibers such as glass fibers, carbon fibers and aramid fibers, fillers, impact modifiers, antioxidants, stabilizers, flame retardants, reheating aids, crystallization aids, oxygen scavengers, plasticizers, flexibilizers, anti-fogging agents, nucleating agents, foaming agents, mold release agents, and combinations thereof. The phenolic blocks and/or reactive functionalized phenolics may be cured by any of the methods and chemistries described herein.

The following exemplary embodiments relate to the specific compounds shown in Scheme 1, but the methods described below apply to all embodiments of the invention.

The neat (meth)acrylic ester products (Products 3, 4, 6, & 7) can be treated with a free-radical initiator (for example cumene hydroperoxide and methyl ethyl ketone peroxide) at a concentration of preferably 0.5-8.0 wt % and most preferably 1.0-3.0 wt % in order to induce curing of the resin to form a novel polymer. Curing of resins can be accomplished with or without a promoter, for example cobalt naphthenate and dimethyl aniline, to accelerate gel time preferably in concentrations of 0.10-1.5 wt %, most preferably 0.25-0.5 wt %. Cure temperatures for substituted bisphenol resins can range from preferably 20-85° C., but most preferably 25-60° C. and preferably post-cured at 100-250° C., but most preferably from 120-180° C. The novel materials have comparable properties to commercial (meth)acrylic ester derived polymers and exhibit similar stiffness, toughness and $T_g$.

The substituted bisphenol (meth)acrylated products (Products 3, 4, 6, & 7) can be blended with a reactive diluents (including, but not limited to: styrene, methacrylated lauric acid, and furfuryl methacrylate) to produce novel resin systems. Typically the composition is 30-90% wt % substituted bisphenol (meth)acrylic ester and 10-70 wt % reactive diluent, more typically 50-75 wt % substituted bisphenol (meth)acrylic ester and 25-50 wt % reactive diluent. The inventors have found these resins to have very low viscosities that would make them ideal for liquid molding, composite layups and vacuum assisted resin transfer molding (VARTM) processing as well as a wide range of other applications. These resins can be cured using a free-radical initiator, in the presence or absence of a promoter, to produce BGF co-polymers that have properties similar to polymeric materials produced by existing commercial processes, providing equivalent stiffness, toughness and $T_g$. The polymer produced from BGF dimethacrylate blended with 50 wt % styrene was found to have a $T_g$ of 186° C. by DSC at 10° C./min, and a maximum degradation temperature of 380° C. by TGA in nitrogen at 10° C./min. Substituted bisphenol UPE (Product 8) resin systems can be blended with olefinically unsaturated reactive diluents (including, but not limited to: styrene, methacrylated lauric acid, and methyl methacrylate) to produce novel resin systems where the composition is 30-90 wt % Product 8 and 10-70 wt % reactive diluent, but most preferably 50-75 wt % Product 8 and 25-50 wt % reactive diluent. These resins have demonstrated viscosities amenable to liquid molding, composite layups, VARTM processing as well as a wide range of other applications. The blended Product 8 resin can be treated with a free-radical initiator (for example cumene hydroperoxide and methyl ethyl ketone peroxide) at a concentration of preferably 0.5-8.0 wt % and most preferably 1.0-3.0 wt % in order to induce curing of the resin to form a novel thermoset polymer. Curing of resins can be accomplished with or without a promoter, for example cobalt naphthenate and dimethyl aniline, to accelerate gel time preferably in concentrations of 0.10-1.5 wt %, but most preferably 0.25-0.75 wt %. Cure temperatures for these UPE resins can range from preferably 20-85° C., but most preferably 25-60° C. and post-cured at 100-200° C., but most preferably from 120-180° C.

EXAMPLES

Example 1—Synthesis of Bisguaiacol F (BGF) with Vanillyl Alcohol and Guaiacol A 500 mL 3-neck round bottom flask equipped with overhead mechanical mixer, reflux condenser, inlet for dry argon gas, and thermometer. The flask was charged with 93.10 g guaiacol (0.75 mol) and 46.25 g vanillyl alcohol (0.30 mol). The mixture was allowed to reflux for 2 hours at 60° C. Next, 13.94 g DOWEX DR2030 hydrogen catalyst was slowly added with continuous mixing. The reaction was allowed to continue overnight at 60° C. for a total of 15 hours. The product was removed from heat and stirring and allowed to cool to room temperature. The resulting oil was dissolved in dichloromethane. The catalyst was removed via vacuum filtration and the filtrate was washed with deionized water. The organic phase was extracted three times, dried with anhydrous sodium sulfate, and concentrated under vacuum. Excess guaiacol was removed from the mixture via vacuum distillation leaving behind a solid BGF product with a yield of 72%. Further purification was carried out on a hexanes/ethyl acetate column. The product was characterized by $^1$H-NMR, $^{13}$C-NMR, and HRMS.

Example 2—Synthesis of Bisguaiacol F with Vanillyl Alcohol and Guaiacol in a Two Phase System A 250 mL round bottom flask was equipped with a magnetic stir bar and a reflux condenser. The flask was charged with 10.9 mL guaiacol (0.10 mol), 10.0 g vanillyl alcohol (0.06 mol), 200 mL water, and 7.34 g DOWEX DR-2030 hydrogen catalyst. The reaction proceeded under reflux for 6 hours then allowed to cool to room temperature. Then, the catalyst was removed using a Buchner funnel and washed with dichloromethane. Additional dichloromethane was added to the remaining two phase system to extract the organic phase. The organic phase was dried with anhydrous sodium sulfate, and concentrated under vacuum. The solid bisguaiacol F product was purified through recrystallization from heptane, resulting in an 82.0 mol % p,p-BGF product.

Example 3—Synthesis of Bisguaiacol F with Vanillyl Alcohol and Guaiacol in a Two Phase System A 250 mL round bottom flask was equipped with a magnetic stir bar and a reflux condenser. The flask was charged with 12.10 g guaiacol (0.097 mol), 10.0 g vanillyl alcohol (0.065 mol), 200 mL water, and 7.34 g DOWEX DR-2030 hydrogen catalyst. The reaction proceeded under reflux for 6 hours then allowed to cool to room temperature. Then, the catalyst was removed using a Buchner funnel and washed with dichloromethane. Additional dichloromethane was added to the remaining two phase system to extract the organic phase. The organic phase was dried with anhydrous sodium sulfate, and concentrated under vacuum and contained 5 mol % oligomers. The solid bisguaiacol F product was purified through recrystallization from heptane, resulting in a 78.8 mol % p,p-BGF product.

Example 4—Synthesis of Bisguaiacol F with Vanillyl Alcohol and Guaiacol in a Two Phase System A 250 mL round bottom flask was equipped with a magnetic stir bar and a reflux condenser. The flask was charged with 12.21 g guaiacol (0.098 mol), 10.00 g vanillyl alcohol (0.065 mol), 150 mL water, and 7.36 g DOWEX DR-2030 hydrogen catalyst. The reaction proceeded under reflux for 6 hours then allowed to cool to room temperature. Then, the catalyst was removed using a Buchner funnel and washed with dichloromethane. Additional dichloromethane was added to the remaining two phase system to extract the organic phase. The organic phase was dried with anhydrous sodium sulfate, and concentrated under vacuum and contained 5 mol % oligomers. The solid bisguaiacol F product was purified through recrystallization from heptane, resulting in an 87.4 mol % p,p-BGF product.

Example 5—Synthesis of Bisguaiacol F with Vanillyl Alcohol and Guaiacol in a Two Phase System A 250 mL round bottom flask was equipped with a magnetic stir bar and a reflux condenser. The flask was charged with 24.42 g guaiacol (0.20 mol), 20.00 g vanillyl alcohol (0.13 mol), 50 mL water, and 10.60 g DOWEX DR-2030 hydrogen catalyst. The reaction proceeded under reflux for 5.5 hours then allowed to cool to room temperature. Then, the catalyst was removed using a Buchner funnel and washed with dichloromethane. Additional dichloromethane was added to the remaining two phase system to extract the organic phase. The organic phase was dried with anhydrous sodium sulfate, and concentrated under vacuum. The solid BGF product was purified through recrystallization from heptane, resulting in a 45.9 mol % p,p-BGF product.

Example 6—Synthesis of Bisguaiacol F with Vanillyl Alcohol and Guaiacol in a Two Phase System A 250 mL round bottom flask was equipped with a magnetic stir bar. The flask was charged with 26.64 g guaiacol (0.21 mol), 20.00 g vanillyl alcohol (0.13 mol), 100 mL water, and 2.00 g DOWEX DR-2030 hydrogen catalyst. The reaction proceeded at 85° C. for 8 hours then allowed to cool to room temperature. Then, the catalyst was removed using a Buchner funnel and washed with 250 mL dichloromethane. The organic phase was extracted from the organic phase, then the organic phase was dried with anhydrous sodium sulfate, and concentrated under vacuum. The solid BGF product was purified through recrystallization from heptane.

Example 7—Synthesis of Bisguaiacol F with Vanillyl Alcohol and Guaiacol in a Two Phase System A 250 mL round bottom flask was equipped with a magnetic stir bar. The flask was charged with 24.42 g guaiacol (0.20 mol), 20.30 g vanillyl alcohol (0.13 mol), 100 mL water, and 4.00 g DOWEX DR-2030 hydrogen catalyst. The reaction proceeded at 70° C. for 6 hours then allowed to cool to room temperature. Then, the catalyst was removed using a Buchner funnel and washed with 250 mL dichloromethane. The organic phase was extracted from the organic phase, then the organic phase was dried with anhydrous sodium sulfate, and concentrated under vacuum. The solid BGF product was purified through recrystallization from heptane.

Example 8—Synthesis of Bisguaiacol F with Vanillyl Alcohol and Guaiacol

A 500 mL round bottom flask was equipped with a magnetic stir bar. The flask was charged with 178.81 g guaiacol (1.44 mol), 50.12 g vanillyl alcohol (0.32 mol), and 5.02 g DOWEX DR-2030 hydrogen catalyst. The mixture was then sparged for 30 min with dry argon. The reaction proceeded at 75° C. for 45 minutes then allowed to cool to room temperature. Then, the catalyst was removed using a Buchner funnel and washed with 50 mL acetone. The unreacted guaiacol and water produced was removed by vacuum distillation. The solid BGF product was purified through recrystallization from heptane, resulting in a 69.9 mol % p,p-BGF product.

Example 9—Synthesis of Bisguaiacol F with Vanillyl Alcohol and Guaiacol

A 250 mL round bottom flask was equipped with a magnetic stir bar. The flask was charged with 108.78 g guaiacol (0.88 mol), 30.00 g vanillyl alcohol (0.19 mol), and 1.50 g DOWEX DR-2030 hydrogen catalyst. The mixture was then sparged for 35 min with dry argon. The reaction proceeded at 75° C. for 30 minutes then allowed to cool to room temperature. Then, the catalyst was removed using a Buchner funnel and washed with 50 mL acetone. The acetone, unreacted guaiacol, and water produced were removed by vacuum distillation. The solid BGF product was purified through recrystallization from heptane, resulting in a 30 mol % yield.

Example 10—Synthesis of Bisguaiacol F with Vanillyl Alcohol and Guaiacol

A 250 mL round bottom flask was equipped with a magnetic stir bar. The flask was charged with 73.26 g guaiacol (0.59 mol), 20.00 g vanillyl alcohol (0.13 mol), and 2.03 g DOWEX DR-2030 hydrogen catalyst. The mixture was then sparged for 30 min with dry argon. The reaction proceeded at 75° C. for 35 minutes. Then, the catalyst was removed from the hot reaction mixture using a Buchner funnel. The unreacted guaiacol and water produced was removed by vacuum distillation. The solid BGF product was purified through recrystallization from heptane to produce a product containing 18.0 mol % higher molecular weight oligomers and a 73.4 mol % p,p-BGF.

Example 11—Synthesis of Bisguaiacol F with Vanillyl Alcohol and Guaiacol

A 500 mL round bottom flask was equipped with a magnetic stir bar. The flask was charged with 366.60 g guaiacol (2.95 mol), 100.50 g vanillyl alcohol (0.65 mol), and 10.26 g DOWEX DR-2030 hydrogen catalyst. The mixture was then sparged for 60 min with dry argon. The reaction proceeded at 70° C. for 50 minutes. Then, the catalyst was removed from the hot reaction mixture using a Buchner funnel. The unreacted guaiacol and water produced was removed by vacuum distillation. The solid BGF product was purified through recrystallization from heptane to produce a product containing 19.4 mol % higher molecular weight oligomers and a 77.2 mol % p,p-BGF.

Example 12—Synthesis of Bisguaiacol F with Vanillyl Alcohol and Guaiacol

A 500 mL round bottom flask was equipped with a magnetic stir bar. The flask was charged with 277.50 g guaiacol (2.24 mol), 75.00 g vanillyl alcohol (0.49 mol), and 7.50 g DOWEX DR-2030 hydrogen catalyst. The mixture was then sparged for 60 min with dry argon. The reaction proceeded at 65° C. for 45 minutes. Then, the catalyst was removed from the hot reaction mixture using a Buchner funnel. The unreacted guaiacol and water produced was removed by vacuum distillation. The solid BGF product was purified through recrystallization from heptane, resulting in 7.6 mol % conversion of vanillyl alcohol, and a 67.7 mol % p,p-BGF product.

Example 13—Synthesis of Bisguaiacol F with Vanillyl Alcohol and Guaiacol with Water Removal A 200 mL 3-neck round bottom flask was equipped with a magnetic stir bar and a Dean-Stark apparatus. The flask was charged with 72.15 g guaiacol (0.43 mol), 20.04 g vanillyl alcohol (0.13 mol), and 2.04 g DOWEX DR-2030 hydrogen catalyst. The mixture was then sparged for 30 min with dry argon. The reaction proceeded at 80° C. for 45 minutes. Then, the catalyst was removed from the hot reaction mixture using a Buchner funnel. The unreacted guaiacol and water produced was removed by vacuum distillation. The solid BGF product was purified through recrystallization from heptane, resulting in an 8.0 mol % conversion of vanillyl alcohol and an 80.0 mol % p,p-BGF product.

Example 14—Synthesis of Bisguaiacol F with Vanillyl Alcohol and Guaiacol with Water Removal A 250 mL round bottom flask was equipped with a magnetic stir bar. The flask was charged with 72.15 g guaiacol (0.58 mol), 20.01 g vanillyl alcohol (0.13 mol), 2.00 g DOWEX DR-2030 hydrogen catalyst, and 5.21 g anhydrous sodium sulfate. The mixture was then sparged for 30 min with dry argon. The reaction proceeded at 80° C. for 45 minutes. Then, the catalyst was removed from the hot reaction mixture using a Buchner funnel. The unreacted guaiacol and water produced was removed by vacuum distillation. The solid BGF product was purified through recrystallization from heptane, resulting in a 67.0 mol % conversion of vanillyl alcohol and a 74.0 mol % p,p-BGF product.

Example 15—Synthesis of Bisguaiacol C with Vanillyl Alcohol and Creosol

A 50 mL round bottom flask was equipped with a magnetic stir bar. The flask was charged with 28.39 g creosol (0.20 mol), 5.00 g vanillyl alcohol (0.032 mol), and 1.05 g DOWEX DR-2030 hydrogen catalyst. The mixture was then sparged for 35 min with dry argon. The reaction proceeded at 80° C. for 1.5 hours. Then, the catalyst was removed from the hot reaction mixture using a Buchner funnel and the product was characterized by $^1$H-NMR, $^{13}$C-NMR. The reaction reached 100 mol % conversion of the vanillyl alcohol with an 86 mol % yield of bisguaiacol C.

Example 16—Synthesis of Bisguaiacol P with Vanillyl Alcohol and Phenol

A 50 mL round bottom flask was equipped with a magnetic stir bar. The flask was charged with 18.36 g phenol (0.30 mol), 4.99 g vanillyl alcohol (0.032 mol), and 1.00 g DOWEX DR-2030 hydrogen catalyst. The mixture was then sparged for 35 min with dry argon. The reaction proceeded at 80° C. for 1.5 hours. Then, the catalyst was removed from the hot reaction mixture using a Buchner funnel and the product was characterized by $^1$H-NMR, $^{13}$C-NMR. The reaction reached 100 mol % conversion of the vanillyl alcohol with an 82 mol % yield of bisguaiacol P, of which 57 mol % was the regioisomer p,p-bisguaiacol P.

Example 17—Synthesis of Bisguaiacol E with Vanillyl Alcohol and 4-Ethylguaiacol

A 50 mL round bottom flask was equipped with a magnetic stir bar. The flask was charged with 29.68 g 4-ethylguaiacol (0.20 mol), 5.04 g vanillyl alcohol (0.033 mol), and 1.00 g DOWEX DR-2030 hydrogen catalyst. The mixture was then sparged for 35 min with dry argon. The reaction proceeded at 80° C. for 1.5 hours. Then, the catalyst was removed from the hot reaction mixture using a Buchner funnel and the product was characterized by $^1$H-NMR, $^{13}$C-NMR. The reaction reached 36 mol % conversion of the vanillyl alcohol with a 30 mol % yield of bisguaiacol E.

Example 18—Synthesis of Bisguaiacol Eu with Vanillyl Alcohol and Eugenol

A 50 mL round bottom flask was equipped with a magnetic stir bar. The flask was charged with 33.17 g eugenol (0.18 mol), 5.02 g vanillyl alcohol (0.032 mol), and 1.04 g DOWEX DR-2030 hydrogen catalyst. The mixture was then sparged for 35 min with dry argon. The reaction proceeded at 80° C. for 1.5 hours. Then, the catalyst was removed from the hot reaction mixture using a Buchner funnel and the product was characterized by $^1$H-NMR, $^{13}$C-NMR. The reaction reached 66 mol % conversion of the vanillyl alcohol with a 35 mol % yield of bisguaiacol Eu.

Example 19—Synthesis of Bisguaiacol PG with Vanillyl Alcohol and 4-Propylguaiacol A 50 mL round bottom flask was equipped with a magnetic stir bar. The flask was charged with 33.17 g 4-propylguaiacol (0.20 mol), 5.03 g vanillyl alcohol (0.033 mol), and 1.07 g DOWEX DR-2030 hydrogen catalyst. The mixture was then sparged for 35 min with dry argon. The reaction proceeded at 80° C. for 1.5 hours. Then, the catalyst was removed from the hot reaction mixture using a Buchner funnel and the product was characterized by $^1$H-NMR, $^{13}$C-NMR. The reaction reached 13 mol % conversion of the vanillyl alcohol with a 13 mol % yield of bisguaiacol PG.

Example 20—Synthesis of Bisguaiacol V with Vanillyl Alcohol and Vanillin

A 50 mL round bottom flask was equipped with a magnetic stir bar. The flask was charged with 27.99 g vanillin (0.18 mol), 5.03 g vanillyl alcohol (0.033 mol), and 0.99 g DOWEX DR-2030 hydrogen catalyst. The mixture was then sparged for 35 min with dry argon. The reaction proceeded at 80° C. for 1.5 hours. Then, the catalyst was removed from the hot reaction mixture using a Buchner funnel and the product was characterized by $^1$H-NMR, $^{13}$C-NMR. The reaction reached 26 mol % conversion of the vanillyl alcohol with a 21 mol % yield of bisguaiacol V.

Example 21—Synthesis of Mixture of Bisguaiacols

A 100 mL round bottom flask was equipped with a magnetic stir bar. The flask was charged with 5.03 g vanillyl alcohol (0.033 mol), 1.54 g phenol (0.016 mol), 3.31 g guaiacol (0.027 mol), 2.01 g 4-ethylguaiacol (0.013 mol), 1.01 g 4-propylguaiacol (0.0061 mol), 1.73 g vanillin (0.011 mol), 1.01 g creosol (0.0073 mol), and 0.50 g DOWEX DR-2030 hydrogen catalyst. The mixture was then sparged for 35 min with dry argon. The reaction proceeded at 75° C. for 1.5 hours. Then, the catalyst was removed from the hot reaction mixture using a Buchner funnel. $^1$H-NMR analysis indicated that the product was a complex mixture of bisguaiacols and oligomers, and that 100 mol % conversion of vanillyl alcohol had been achieved.

Example 22—Synthesis of Bisguaiacol F Using AMBERLYST 15 Hydrogen Form

A 50 mL round bottom flask was equipped with a magnetic stir bar. The flask was charged with 5.00 g vanillyl alcohol (0.032 mol), 20.64 g guaiacol (0.17 mol), and 0.51 g AMBERLYST 15 hydrogen form (4.7 meq/g) catalyst. The mixture was then sparged for 20 min with dry argon. The reaction proceeded at 75° C. for 0.5 hours. Then, the catalyst was removed from the hot reaction mixture using a Buchner funnel and characterized by $^1$H-NMR and $^{13}$C-NMR. A BGF yield of 5.0 mol % was achieved.

Example 23—Synthesis of Bisguaiacol F Using AMBERLYST 15 Hydrogen Form

A 50 mL round bottom flask was equipped with a magnetic stir bar. The flask was charged with 5.02 g vanillyl alcohol (0.032 mol), 20.64 g guaiacol (0.17 mol), and 0.49 g AMBERLYST 15 hydrogen form (4.7 meq/g) catalyst. The mixture was then sparged for 20 min with dry argon. The reaction proceeded at 75° C. for 1.0 hours. Then, the catalyst was removed from the hot reaction mixture using a Buchner funnel and characterized by $^1$H-NMR and $^{13}$C-NMR. A BGF yield of 13.0 mol % was achieved.

Example 24—Synthesis of Bisguaiacol F Using AMBERLYST 15 Hydrogen Form

A 3-neck 500 mL round bottom flask was equipped with a magnetic stir bar. The flask was charged with 75.00 g vanillyl alcohol (0.49 mol), 273.10 g guaiacol (1.98 mol), and 7.50 g AMBERLYST 15 hydrogen form (4.7 meq/g) catalyst. The mixture was then sparged for 40 min with dry argon. The reaction proceeded at 75° C. for 0.33 hour. Then, the catalyst was removed from the hot reaction mixture using a Buchner funnel. The unreacted guaiacol and water produced was removed by vacuum distillation. The solid BGF product was purified through recrystallization from heptane, resulting in an 81.1 mol % p,p-BGF product.

Example 25—Synthesis of Bisguaiacol F Using AMBERLYST 15 Hydrogen Form

A 500 mL round bottom flask was equipped with a magnetic stir bar. The flask was charged with 75.00 g vanillyl alcohol (0.49 mol), 322.5 g guaiacol (2.6 mol), and 15.00 g AMBERLYST 15 hydrogen form (4.7 meq/g) catalyst. The mixture was then sparged for 60 min with dry argon. The reaction proceeded at 75° C. for 0.33 hour. Then, the catalyst was removed from the hot reaction mixture using a Buchner funnel. The unreacted guaiacol and water produced was removed by vacuum distillation. The solid BGF product was purified through recrystallization from heptane, resulting in a 77.5 mol % p,p-BGF product.

Example 26—Synthesis of Bisguaiacol F Using AMBERLYST 15 Hydrogen Form

A 50 mL round bottom flask was equipped with a magnetic stir bar. The flask was charged with 3.01 g vanillyl alcohol (0.020 mol), 11.29 g guaiacol (0.091 mol), and 1.52 g AMBERLYST 15 hydrogen form (4.7 meq/g) catalyst. The mixture was then sparged for 30 min with dry argon. The reaction proceeded at 75° C. for 1.5 hours. Then, the catalyst was removed from the hot reaction mixture using a Buchner funnel. Then, the catalyst was removed from the hot reaction mixture using a Buchner funnel and characterized by $^1$H-NMR and $^{13}$C-NMR. A 100 mol % conversion of vanillyl alcohol was achieved with a 73.8 mol % p,p-BGF product with 28.0 mol % higher molecular weight oligomers.

Example 27—Synthesis of Bisguaiacol F Using DOWEX Mac-3 Hydrogen Form

A 50 mL round bottom flask was equipped with a magnetic stir bar. The flask was charged with 3.08 g vanillyl alcohol (0.020 mol), 11.29 g guaiacol (0.091 mol), and 1.55 g DOWEX Mac-3 hydrogen form (3.8 meq/g wet weight) catalyst. The mixture was then sparged for 30 min with dry argon. The reaction proceeded at 75° C. for 1.5 hours. Then, the catalyst was removed from the hot reaction mixture using a Buchner funnel and characterized by 1H-NMR and $^{13}$C-NMR. A 5.8 mol % conversion of vanillyl alcohol was achieved with a 57.8 mol % p,p-BGF product.

Example 28—Synthesis of Bisguaiacol F Using DOWEX G26 Hydrogen Form

A 50 mL round bottom flask was equipped with a magnetic stir bar. The flask was charged with 3.01 g vanillyl alcohol (0.020 mol), 11.29 g guaiacol (0.091 mol), and 1.54 g DOWEX G26 hydrogen form (2.0 meq/g wet weight) catalyst. The mixture was then sparged for 30 min with dry argon. The reaction proceeded at 75° C. for 1.5 hours. Then, the catalyst was removed from the hot reaction mixture using a Buchner funnel and characterized by $^1$H-NMR and $^{13}$C-NMR. A 94.4 mol % conversion of vanillyl alcohol was achieved with a 76.4 mol % p,p-BGF product with 27.9 mol % higher molecular weight oligomers.

Example 29—Synthesis of Bisguaiacol F Using DOWEX Marathon C Hydrogen Form

A 50 mL round bottom flask was equipped with a magnetic stir bar. The flask was charged with 3.07 g vanillyl alcohol (0.032 mol), 11.29 g guaiacol (0.091 mol), and 1.51 g DOWEX Marathon C hydrogen form (1.8 meq/g) catalyst. The mixture was then sparged for 30 min with dry argon. The reaction proceeded at 75° C. for 1.5 hours. Then, the catalyst was removed from the hot reaction mixture using a Buchner funnel and characterized by $^1$H-NMR and $^{13}$C-NMR. A 100 mol % conversion of vanillyl alcohol was achieved with a 74.0 mol % p,p-BGF product with 20.0 mol % higher molecular weight oligomers.

Example 30—Synthesis of Vanillyl Alcohol Oligomers

A 50 mL round bottom flask was equipped with a magnetic stir bar. The flask was charged with 5.09 g vanillyl alcohol (0.033 mol), 25 mL deionized water, and 0.51 g AMBERLYST 15 hydrogen form (4.5 meq/g) catalyst. The mixture was then sparged for 30 min with dry argon. The reaction proceeded at 120° C. for 0.5 hours. Then, reaction mixture was dissolved in acetone and the catalyst was removed using a Buchner funnel, then concentrated under reduced pressure. $^1$H-NMR suggests that oligomers have approximately 2-5 repeat units on average with p, o- and p, m-connectivity relative to the hydroxyl groups with molecular weights less than 700 g/mol relative to polystyrene standards.

Example 31—Synthesis of Vanillyl Alcohol Oligomers

A 50 mL round bottom flask was equipped with a magnetic stir bar. The flask was charged with 5.04 g vanillyl alcohol (0.033 mol), 25 mL deionized water, and 0.50 g AMBERLYST 15 hydrogen form (4.5 meq/g) catalyst. The mixture was then sparged for 30 min with dry argon. The reaction proceeded at 120° C. for 1.5 hours. Then, the reaction mixture was dissolved in acetone and the catalyst was removed using a Buchner funnel, then concentrated under reduced pressure. $^1$H-NMR indicated that the resulting oligomers had on average 3-13 repeat units with p,o- and p,m-connectivity relative to the hydroxyl groups, with molecular weights between 500-18,000 g/mol relative to polystyrene standards.

Example 32—Synthesis of Crosslinked Polymer from Vanillyl Alcohol

A 50 mL round bottom flask was equipped with a magnetic stir bar and a reflux condenser. The flask was charged with 2.00 g vanillyl alcohol (0.013 mol), 10 mL deionized water, and 0.20 g DOWEX DR-2030 hydrogen form (4.5 meq/g) catalyst. The mixture was then sparged for 30 min with dry argon. The reaction proceeded at 120° C. for 20 hours. The resulting polymer was dried of water, and was not soluble in any solvent, indicating the synthesis of a crosslinked polymer of unmeasurable molecular weight or a linear or branched polymer of high molecular weight.

Example 33—Synthesis of Bisguaiacol F Dimethacrylate Using Methacrylic Anhydride A 100 mL round bottom flask was equipped with a magnetic stir bar. The flask was charged with 1.34 g BGF (0.0052 mol), 1.79 g methacrylic anhydride (0.011 mol), and 0.065 g 4-(dimethylamino)pyridine (0.00053 mol). The flask was sparged with dry argon gas for 30 minutes then placed in a 75° C. oil bath equipped with magnetic stirring and allowed to proceed for 48 hours. The reaction mixture was allowed to cool to room temperature then was dissolved in 100 mL dichloromethane. The organic phase was extracted two times each with concentrated sodium bicarbonate solution, 1.0 M sodium hydroxide, 1.0 N hydrochloric acid, and deionized water sequentially, dried with anhydrous sodium sulfate, then concentrated under vacuum. The product was characterized by $^1$H-NMR, $^{13}$C-NMR.

Example 34—Synthesis of Vanillyl Alcohol Dimethacrylate Using Methacrylic Anhydride A round bottom flask is equipped with a magnetic stir bar. The flask is charged with vanillyl alcohol (1 eq), methacrylic anhydride (2.1 eq), and 4-(dimethylamino)pyridine (0.10). The flask is sparged with dry argon gas for 30 minutes then placed in a 75° C. oil bath equipped with magnetic stirring and allowed to proceed for 48 hours. The reaction mixture is allowed to cool to room temperature then dissolved in dichloromethane. The organic phase is extracted two times each with concentrated sodium bicarbonate solution, 1.0 M sodium hydroxide, 1.0 N hydrochloric acid, and deionized water sequentially, dried with anhydrous sodium sulfate, then concentrated under vacuum. The product is obtained through silica gel chromatography.

Example 35—Synthesis of Bisguaiacol F Dimethacrylate Using Methacryloyl Chloride A 3-neck 250 mL round bottom flask was equipped with a magnetic stir bar, addition funnel, and a thermometer. The below 0° C. chilled flask was charged with 5.08 g BGF (0.020 mol), 7.98 g triethylamine (0.079 mol), and 125 mL dichloromethane. The flask was sparged with dry argon gas for 40 minutes then placed in an ice bath and kept below 0° C. as 8.02 g methacryloyl chloride (0.077 mol) dissolved in 50 mL of dichloromethane was added dropwise through the addition funnel. The reaction mixture was allowed to warm to room temperature overnight after the full addition of methacryloyl chloride. The organic phase was extracted three times each with concentrated sodium bicarbonate solution, 1.0 M sodium hydroxide, 1.0 N hydrochloric acid, and deionized water sequentially, dried with anhydrous sodium sulfate, then concentrated under vacuum. The product was characterized by $^1$H-NMR, $^{13}$C-NMR.

Example 36—Synthesis of Vanillyl Alcohol Dimethacrylate Using Methacryloyl Chloride A 3-neck round bottom flask is equipped with a magnetic stir bar, addition funnel, and a thermometer. The below 0° C. chilled flask is charged with vanillyl alcohol (1 eq), triethylamine (4 eq), and dichloromethane. The flask is sparged with dry argon gas for 40 minutes then placed in an ice bath and kept below 0° C. as methacryloyl chloride (4 eq) dissolved in dichloromethane is added dropwise through the addition funnel. The reaction mixture is allowed to warm to room temperature overnight after the full addition of meth-acryloyl chloride. The organic phase is extracted three times each with concentrated sodium bicarbonate solution, 1.0 M sodium hydroxide, 1.0 N hydrochloric acid, and deionized water sequentially, dried with anhydrous sodium sulfate, then concentrated under vacuum. The product is obtained through silica gel chromatography.

Example 37—Curing of Bisguaiacol F Dimethacrylate Thermoset

Two 3 mL scintillation vials were sprayed with release agent. 1.46 g BGF dimethacrylate, 1.20 g styrene, and 0.052 g Trigonox 239 as the initiator were mixed and degassed under reduced pressure. The mixture was then split between the two prepared vials equally and degassed again under reduced pressure. The samples were cured under an inert atmosphere at 90° C. for 2.0 hours then post-cured at 120° C. for 2.0 hours. The thermoset was characterized by thermogravimetric analysis (TGA) and differential scanning calorimetry (DSC).

Example 38—Curing of Vanillyl Alcohol Dimethacrylate Thermoset

Two 3 mL scintillation vials are sprayed with release agent. A 1:1 wt ratio of vanillyl alcohol dimethacrylate and styrene is mixed with 1.2 wt % Trigonox 239 as the initiator are mixed and degassed under reduced pressure. The mixture is then split between the two prepared vials equally and degassed again under reduced pressure. The samples are cured under an inert atmosphere at 90° C. for 2.0 hours then post-cured at 120° C. for 2.0 hours.

Example 39—Synthesis of Bisguaiacol F Diacrylate Using Acryloyl Chloride

A 3-neck 250 mL round bottom flask was equipped with a magnetic stir bar, addition funnel, and a thermometer. The below 0° C. chilled flask was charged with 5.01 g BGF (0.019 mol), 7.98 g triethylamine (0.079 mol), and 125 mL dichloromethane. The flask was sparged with dry argon gas for 40 minutes then placed in an ice bath and kept below 0° C. as 8.36 g acryloyl chloride (0.092 mol) dissolved in 50 mL of dichloromethane was added dropwise through the addition funnel. The reaction mixture was allowed to warm to room temperature overnight after the full addition of acryloyl chloride. The organic phase was extracted three times each with concentrated sodium bicarbonate solution, 1.0 M sodium hydroxide, 1.0 N hydrochloric acid, and deionized water sequentially, dried with anhydrous sodium sulfate, then concentrated under vacuum. The product was characterized by $^1$H-NMR, $^{13}$C-NMR.

Example 40—Synthesis of Vanillyl Alcohol Diacrylate Using Acryloyl Chloride

A 3-neck 250 mL round bottom flask is equipped with a magnetic stir bar, addition funnel, and a thermometer. The below 0° C. chilled flask is charged with vanillyl alcohol (1 eq), triethylamine (4 eq), and dichloromethane. The flask is sparged with dry argon gas for 40 minutes then placed in an ice bath and kept below 0° C. as acryloyl chloride (4 mol) dissolved in dichloromethane is added dropwise through the addition funnel. The reaction mixture is allowed to warm to room temperature overnight after the full addition of acryloyl chloride. The organic phase is extracted three times each with concentrated sodium bicarbonate solution, 1.0 M

Example 41—Synthesis of Diglycidyl Ether of Bisguaiacol F

A 50 mL round bottom flask was equipped with a magnetic stir bar and constant pressure dropping funnel. The flask was charged with 1.72 g bisguaiacol F (6.60 mmol), 9.16 g epichlorohydrin (9.90 mmol), and 0.21 g tetrabutylammonium bromide (0.70 mmol). The mixture was stirred vigorously at room temperature overnight. After 15 hours, the mixture was placed in an ice bath and allowed to cool below 10° C. Next, 4.0 g of a 33% w/w aqueous solution of sodium hydroxide was added drop wise with constant stirring. The mixture was left to react overnight with the ice bath melting. The resulting epoxy brine was dissolved in dichloromethane and washed with deionized water. The organic phase was extracted, concentrated under reduced pressure, and placed in a vacuum oven overnight at 60° C. The epoxy yield was 84 wt %. The epoxy structure was confirmed via $^1$H-NMR, $^{13}$C-NMR, and HRMS. The diglycidyl ether of bisguaiacol F was a white solid with a melting point of 106-109° C. The epoxy equivalent weight was determined to be 204 g/eq. according to ASTM D1652.

Example 42—Synthesis of Diglycidyl Ether of Bisguaiacol F

A 250 mL 3-neck round bottom flask was equipped with reflux condenser, constant pressure dropping funnel, inlet for dry argon gas, magnetic stir bar, and thermometer. The flask was charged with 7.11 g bisguaiacol F (26.9 mmol), 25.30 g epichlorohydrin (269 mmol), and 0.90 g tetrabutylammonium bromide (2.70 mmol). The flask was heated to 40° C. for 3 hours with constant stirring. Then, the mixture was placed in an ice bath and allowed to cool below 10° C. Next, 9.60 mL of a 40% w/w aqueous solution of sodium hydroxide was added drop wise with constant stirring. After the addition of the sodium hydroxide the mixture was removed from ice bath and left to react overnight at room temperature. The resulting epoxy brine was dissolved in dichloromethane and washed with deionized water. The organic phase was extracted three times, concentrated under reduced pressure, and placed in a vacuum oven overnight. The epoxy product yield was 73 wt %. The epoxy structure was confirmed via $^1$H-NMR, $^{13}$C-NMR, and HRMS. The diglycidyl ether of bisguaiacol F was a white solid with a melting point of 104-109° C. The resin was further purified on a hexanes/ethyl acetate column. The epoxy equivalent weight was determined to be 193 g/eq. according to ASTM D-1652.

Example 43—Synthesis of Vinyl Ester of Diglycidyl Ether of Vanillyl Alcohol

A round bottom flask is equipped with a magnetic stir bar. The flask is charged with vanillyl alcohol (1 eq), 9.80 g methacrylic acid (10 eq), and 1 wt % AMC-2 catalyst. The flask is placed in a 65° C. oil bath equipped with magnetic stirring and the reaction is allowed to proceed for 10 hours or until an acid number of less than 5 is achieved based on ASTM D1980.

Example 44—Synthesis of Vinyl Ester of Diglycidyl Ether of Bisguaiacol F

A round bottom flask is equipped with a magnetic stir bar. The flask is charged with bisguaiacol F (1 eq), methacrylic acid (10 eq), and 1 wt % AMC-2 catalyst. The flask is placed in a 65° C. oil bath equipped with magnetic stirring and the reaction is allowed to proceed for 10 hours or until an acid number of less than 5 is achieved based on ASTM D1980.

Example 45—Cure of Diglycidyl Ether of Bisguaiacol F with a Diamine 0.5229 g of diglycidyl ether of bisguaiacol F was melted at 110° C. in a glass beaker. Then, 0.1335 g of AMICURE PACM (4,4'-methylenebiscyclohexamine) was added to the liquefied epoxy resin and mixed vigorously with a glass stir rod. The sample was degassed in a vacuum oven for two minutes to remove any trapped air. The epoxy/amine resin was cured in an oven at 110° C. for 2 hours and then at 160° C. for an additional 1 hour. The sample was post cured for 10 hours at 180° C.

Example 46—Synthesis of Bisguaiacol Polycarbonates

Bisguaiacol F (1.0034 g) was added to a 100 mL round bottom flask equipped with a magnetic stir bar. The flask sealed with a rubber septum and purged with dry argon gas. p-Nitrochloroformate (0.8094 g) was added to another 100 mL round bottom flask equipped with a magnetic stir bar. The flask was sealed with a rubber septum and purged with dry argon gas. Dry acetonitrile (50 mL) was transferred to each of the flasks containing bisguaiacol F and p-nitrochloroformate under continuous argon flow. 4-(Dimethylamino)pyridine (DMAP, 0.0282 g) and triethylamine (1.000 mL) were added to a 300 mL three-neck round bottom flask equipped with a magnetic stir bar. The flask was sealed with a rubber septum and purged with dry argon gas. Dry acetonitrile (30 mL) was transferred to the three-neck round bottom flask containing DMAP and triethylamine under continuous argon flow. All flasks were mixed vigorously. The bisguaiacol F in acetonitrile and the p-nitrochloroformate in acetonitrile solutions were transferred to the three neck round bottom under continuous argon flow in approximately 25 mL aliquots for a total of 8 transfers. The sealed reaction mixture was allowed to stir for one hour at room temperature. After one hour, the reaction was opened to the atmosphere and allowed to reflux at 83° C. for 4 hours. Then the reaction was allowed to continue for an additional 43 hours at 53° C. After a total of 48 hours, the reaction was quenched by the addition of 300 mL methanol. The number average and weight average molecular weight based on GPC are 9,500 and 13,200 g/mol, respectively with a dispersity of 1.39 relative to polystyrene standards.

Example 47—Reaction of BGF with Toluene Diisocyanate to Form Polyurethanes

Purified BGF (1.0156 g, 3.9018 mmol) and toluene diisocyanate (TDI, 0.6675 g, 3.8318 mmol) were dissolved in tetrahydrofuran (50 mL) before adding trimethylamine (TEA, 31.0 mg, 0.3064 mmol) and stirring for 72 hours. The solvent was removed under reduced pressure and the off white powder (1.583 g, 94.1% yield, $M_W$=8,000-12,000 g/mol relative to polystyrene standards) was characterized by $^1$H-NMR, GPC and DSC.

[Previous paragraph continuation at top of page:] sodium hydroxide, 1.0 N hydrochloric acid, and deionized water sequentially, dried with anhydrous sodium sulfate, then concentrated under vacuum. The product is obtained through silica gel chromatography.

Example 48—Reaction of BGF with Maleic Anhydride and Phthalic Anhydride to Form Unsaturated Polyester Resins BGF (9.634 g 37.01 mmol), diethylene glycol (DEG, 3.93 g, 37.03 mmol), maleic anhydride (2.177 g, 22.20 mmol) and phthalic anhydride (7.67 g, 51.78 mmol) were suspended in toluene (60 mL) and melted together at 55° C. before adding p-toluenesulfonic acid (1.40 g, 7.35 mmol) and refluxed with the aid of a Dean-Stark attachment. The progress of the reaction was monitored by Acid Number (AN) titration. Once the extent of reaction was between 0.930-0.975, the reaction was fitted with a vacuum distillation adapter and distilled at ambient pressure for 2 hours and then under reduced pressure (−68 mbar) for 1.5 hours. Hydroquinone was added to the molten resin and allowed to stir and cool for 15 minutes before placing in a vacuum oven at 55° C. at −30 mbar for 18 hours to remove remaining toluene. Resins appeared as dark amber semi-solid (21.9 g, $M_W$=2,400-3,200 g/mol relative to polystyrene standards) and was characterized by $^1$H-NMR, GPC.

What is claimed is:

1. A compound according to structure 4,

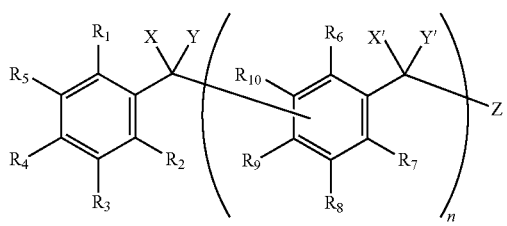

4 wherein n has a value from 0 to 48 and Z is a benzene ring bearing substituents $R_{11}$-$R_{15}$;

when n=0:
one of $R_1$-$R_5$ is alkoxy, one of $R_1$-$R_5$ is an ester-containing group derived from a hydroxyl group directly bonded to the benzene ring, and the remaining $R_1$-$R_5$ are hydrogen atoms;
one of $R_{11\text{-}15}$ is alkoxy, one of $R_{11}$-$R_{15}$ is an ether group derived from a hydroxyl group directly bonded to the benzene ring, and the remaining $R_{11}$-$R_{15}$ are hydrogen atoms; and
X and Y are hydrogen atoms;

when n=1-48:
one of $R_1$-$R_5$ is alkoxy, one of $R_1$-$R_5$ is a hydroxyl group, an ester-containing group derived from a hydroxyl group directly bonded to the benzene ring or an ether group derived from a hydroxyl group directly bonded to the benzene ring, and the remaining $R_1$-$R_5$ are hydrogen atoms;
one of $R_6$-$R_{10}$ is a direct bond to the preceding CXY group or CX'Y' group, one of $R_6$-$R_{10}$ is alkoxy, one of $R_6$-$R_{10}$ is a hydroxyl group, an ester-containing group derived from a hydroxyl group directly bonded to the benzene ring or an ether group derived from a hydroxyl group directly bonded to the benzene ring, and the remaining $R_6$-$R_{10}$ are hydrogen atoms;
one of $R_{11}$-$R_{15}$ is alkoxy, one of $R_{11}$-$R_{15}$ is a hydroxyl group, an ester-containing group derived from a hydroxyl group directly bonded to the benzene ring or an ether group derived from a hydroxyl group directly bonded to the benzene ring, and the remaining $R_{11}$-$R_{15}$ are hydrogen atoms;
at least one of $R_1$-$R_{15}$ is an ester-containing group derived from a hydroxyl group directly bonded to the benzene ring;
at least one of $R_1$-$R_{15}$ is an ether group derived from a hydroxyl group directly boned to the benzene ring; and
X, X', Y, and Y' are hydrogen atoms;
wherein the ether group is glycidyl ether; and
wherein the ester-containing group is (meth)acrylate or 3-(meth)acryloyloxy-2-hydroxy-1-propoxy.

2. A composition comprising the reaction product of the compound according to claim 1 with an epoxy curing agent.

3. The composition according to claim 2, further comprising one or more materials selected from the group consisting of fibers, reinforcing materials, clays, silicates, fillers and whiskers.

4. The composition according to claim 2, further comprising one or more materials selected from the group consisting of nanofibers, nanoclays, nanofillers, and nanowhiskers.

5. The composition according to claim 2, further comprising one or more materials selected from the group consisting of solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

6. The compound according to claim 1, wherein n=0.

7. A composition comprising the reaction product of the compound according to claim 6 with an epoxy curing agent.

8. The composition according to claim 7, further comprising one or more additives selected from the group consisting of fibers, reinforcing materials, clays, silicates, fillers, whiskers, nanofibers, nanoclays, nanofillers, nanowhiskers, solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

9. The compound according to claim 1, wherein the ester-containing group is 3-(meth)acryloyloxy-2-hydroxy-1-propoxy.

10. A composition comprising the compound according to claim 9, homopolymerized or copolymerized through chain growth polymerization.

11. The composition according to claim 10, further comprising one or more materials selected from the group consisting of fibers, reinforcing materials, clays, silicates, fillers, and whiskers.

12. The composition according to claim 10, further comprising one or more materials selected from the group consisting of nanofibers, nanoclays, nanofillers, and nanowhiskers.

13. The composition according to claim 10, further comprising one or more materials selected from the group consisting of solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

14. The compound according to claim 9, wherein n=0.

15. A composition comprising the compound according to claim 14, homopolymerized or copolymerized through chain growth polymerization.

16. The composition according to claim 15, further comprising one or more additives selected from the group consisting of fibers, reinforcing materials, clays, silicates, fillers, whiskers, nanofibers, nanoclays, nanofillers, nanowhiskers, solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

17. The compound according to claim 1, wherein the ester-containing group is (meth)acrylate.

18. A composition comprising the compound according to claim 17, homopolymerized or copolymerized through chain growth polymerization.

19. The composition according to claim 18, further comprising one or more materials selected from the group consisting of fibers, reinforcing materials, clays, silicates, fillers and whiskers.

20. The composition according to claim 18, further comprising one or more materials selected from the group consisting of nanofibers, nanoclays, nanofillers, and nanowhiskers.

21. The composition according to claim 18, further comprising one or more materials selected from the group consisting of solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

22. The compound according to claim 17, wherein n=0.

23. A composition comprising the compound according to claim 22, homopolymerized or copolymerized through chain growth polymerization.

24. The composition according to claim 23, further comprising one or more additives selected from the group consisting of fibers, reinforcing materials, clays, silicates, fillers, whiskers, nanofibers, nanoclays, nanofillers, nanowhiskers, solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

25. A compound having the following structure:

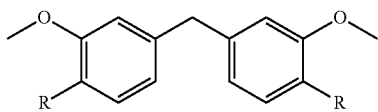

wherein R is an ester-containing group derived from a hydroxyl group directly bonded to the benzene ring or an ether group derived from a hydroxyl group directly bonded to the benzene ring;

wherein the ether group is glycidyl ether; and
wherein the ester-containing group is (meth)acrylate or 3-(meth)acryloyloxy-2-hydroxy-1-propoxy.

26. The compound according to claim 25, wherein R is glycidyl ether.

27. A composition comprising the reaction product of the compound according to claim 26 with an epoxy curing agent.

28. The composition according to claim 27, further comprising one or more additives selected from the group consisting of fibers, reinforcing materials, clays, silicates, fillers, whiskers, nanofibers, nanoclays, nanofillers, nanowhiskers, solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

29. The compound according to claim 25, wherein R is (meth)acrylate.

30. A composition comprising the compound according to claim 29, homopolymerized or copolymerized through chain growth polymerization.

31. The composition according to claim 30, further comprising one or more additives selected from the group consisting of fibers, reinforcing materials, clays, silicates, fillers, whiskers, nanofibers, nanoclays, nanofillers, nanowhiskers, solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

32. The compound according to claim 25, wherein R is 3-(meth)acryloyloxy-2-hydroxy-1-propoxy.

33. A composition comprising the compound according to claim 32, homopolymerized or copolymerized through chain growth polymerization.

34. The composition according to claim 33, further comprising one or more additives selected from the group consisting of fibers, reinforcing materials, clays, silicates, fillers, whiskers, nanofibers, nanoclays, nanofillers, nanowhiskers, solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

35. A polymer or oligomer selected from the group consisting of:
a first polymer or oligomer having the following structure:

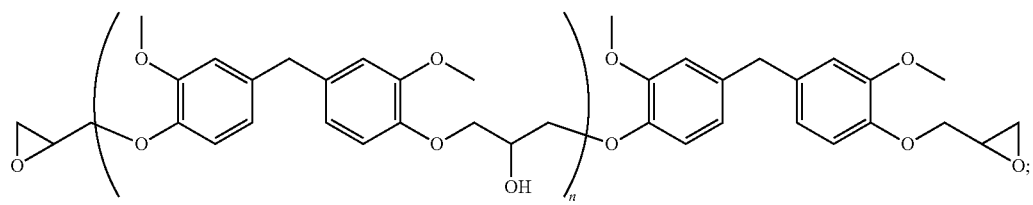

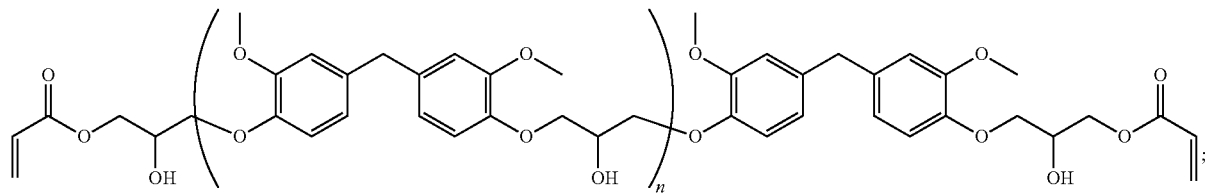

and
a third polymer or oligomer having the following structure:

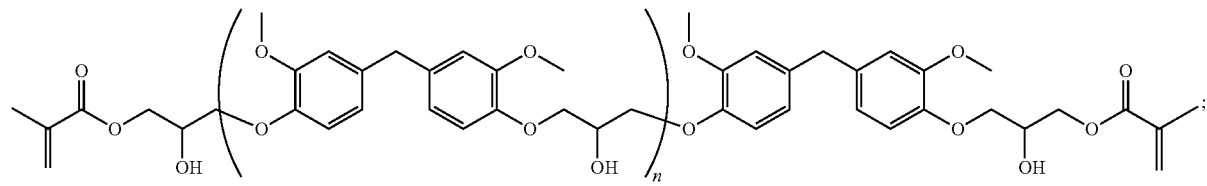

where n=1-24.

36. The polymer or oligomer according to claim 35, which is the first polymer or oligomer.

37. A composition comprising the reaction product of the polymer or oligomer according to claim 36 with an epoxy curing agent.

38. The composition according to claim 37, further comprising one or more additives selected from the group consisting of fibers, reinforcing materials, clays, silicates, fillers, whiskers, nanofibers, nanoclays, nanofillers, nanowhiskers, solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

39. The polymer or oligomer according to claim 35, which is the second polymer or oligomer.

40. A composition comprising units of the polymer or oligomer of claim 39 joined by chain growth polymerization.

41. The composition according to claim 40, further comprising one or more materials selected from the group consisting of fibers, reinforcing materials, clays, silicates, fillers and whiskers.

42. The composition according to claim 40, further comprising one or more materials selected from the group consisting of nanofibers, nanoclays, nanofillers, and nanowhiskers.

43. The composition according to claim 40, further comprising one or more materials selected from the group consisting of solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

44. The polymer or oligomer according to claim 35, which is the third polymer or oligomer.

45. A composition comprising units of the polymer or oligomer of claim 44 joined by chain growth polymerization.

46. The composition according to claim 45, further comprising one or more additives selected from the group consisting of fibers, reinforcing materials, clays, silicates, fillers, whiskers, nanofibers, nanoclays, nanofillers, nanowhiskers, solvents, flow additives, pigments, corrosion inhibitors, film formers, defoamers, coupling agents, antioxidants, stabilizers, flame retardants, reheating aids, plasticizers, flexibilizers, anti-fogging agents, and nucleating agents.

* * * * *

UNITED STATES PATENT AND TRADEMARK OFFICE
CERTIFICATE OF CORRECTION

PATENT NO. : 10,723,684 B2
APPLICATION NO. : 15/313656
DATED : July 28, 2020
INVENTOR(S) : Kaleigh Havery Reno Page 1 of 1

It is certified that error appears in the above-identified patent and that said Letters Patent is hereby corrected as shown below:

In the Claims

In Claim 35, Column 33 Line 1 please add -- a second polymer or oligomer having the following structure; -- above the second structure.

Signed and Sealed this
Twenty-ninth Day of September, 2020

Andrei Iancu
*Director of the United States Patent and Trademark Office*